US006317387B1

(12) United States Patent
D'Amaddio et al.

(10) Patent No.: US 6,317,387 B1
(45) Date of Patent: Nov. 13, 2001

(54) METHOD AND APPARATUS FOR INSPECTING A SUBMERGED STRUCTURE

(76) Inventors: Eugene R. D'Amaddio, 2 Olde Forge La., Bourne, MA (US) 02532; Stewart E. Harris, 761 Farm Hill Ct., Walnut Creek, CA (US) 94598; Emile M. Bergeron, 74 Gifford St., Falmouth, MA (US) 02540; Edwin V. Slate, 56 Clear Pond Rd., Falmouth, MA (US) 02556

( * ) Notice: Subject to any disclaimer, the term of this patent is extended or adjusted under 35 U.S.C. 154(b) by 0 days.

(21) Appl. No.: 09/165,426

(22) Filed: Oct. 2, 1998

Related U.S. Application Data
(60) Provisional application No. 60/066,212, filed on Nov. 20, 1997.

(51) Int. Cl.[7] .................................................. B63B 59/00
(52) U.S. Cl. .......................... 367/129; 114/222; 367/131
(58) Field of Search .................................. 367/118, 124, 367/129, 131; 114/222

(56) References Cited

U.S. PATENT DOCUMENTS

| | | |
|---|---|---|
| 3,534,326 | 10/1970 | Glenn . |
| 3,776,574 | 12/1973 | Henderson et al. . |
| 4,088,979 | 5/1978 | Jones et al. . |
| 4,308,600 | 12/1981 | Poupel et al. . |
| 4,981,353 | 1/1991 | Murakawa et al. . |
| 5,047,990 | * 9/1991 | Gafos et al. .......................... 367/118 |
| 5,184,230 | 2/1993 | Watson . |
| 5,249,891 | 10/1993 | Pecue, II . |
| 5,291,025 | 3/1994 | Smith . |
| 5,316,412 | 5/1994 | Sondergard . |
| 5,367,496 | 11/1994 | Sullivan et al. . |
| 5,425,275 | 6/1995 | Lockshaw . |
| 5,444,441 | 8/1995 | Sutton . |
| 5,513,930 | * 5/1996 | Eathorne .............................. 114/222 |
| 5,947,051 | * 9/1999 | Geiger ................................. 114/222 |

FOREIGN PATENT DOCUMENTS

WO 94/23311   10/1994   (WO) .

OTHER PUBLICATIONS

Barbara Fletcher and Stephen Greelish; Precision Automation Of ROV Inspections For The Nuclear Industry; Jan. 16–18, 1995; pp. 79–83; Underwater Intervention 1995, Jan. 16–18, 1995, Westin Galleria Hotel, Houston, TX.

Faila et al., "Hardware Design and Implementation for Underwater Surface Integration" Proc. of the 1996 IEEE/SICE/RJS Int. conf. on Multisensor Fusion and Integration for Intelligent Systems, pp. 815–822, 1996.*

* cited by examiner

*Primary Examiner*—Ian J. Lobo
(74) *Attorney, Agent, or Firm*—Handal & Morofsky

(57) ABSTRACT

The present invention relates to an underwater apparatus, system and method for inspecting and determining the condition of a submerged structure. More particularly the present invention utilizes acoustical devices for the positioning of an inspection vehicle, with respect to the structure to be inspected.

28 Claims, 16 Drawing Sheets

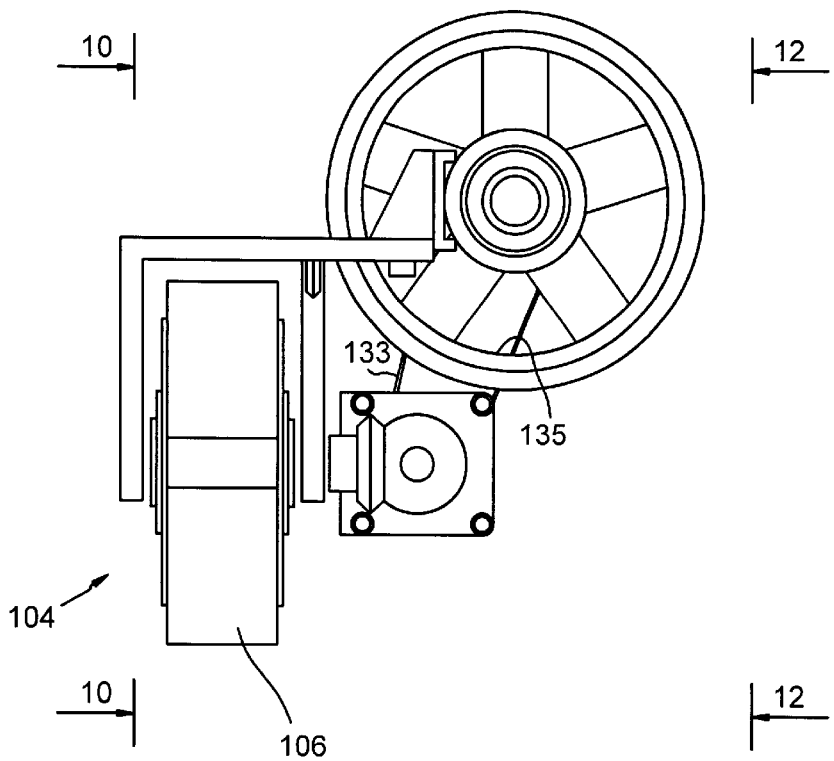
FIGURE 9
FIGURE 10
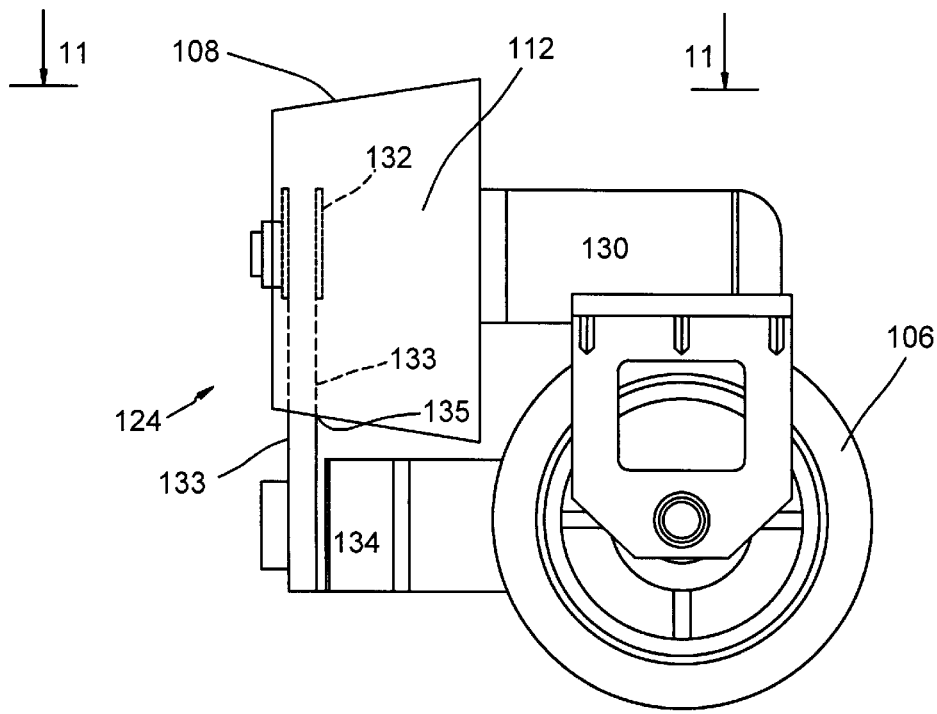

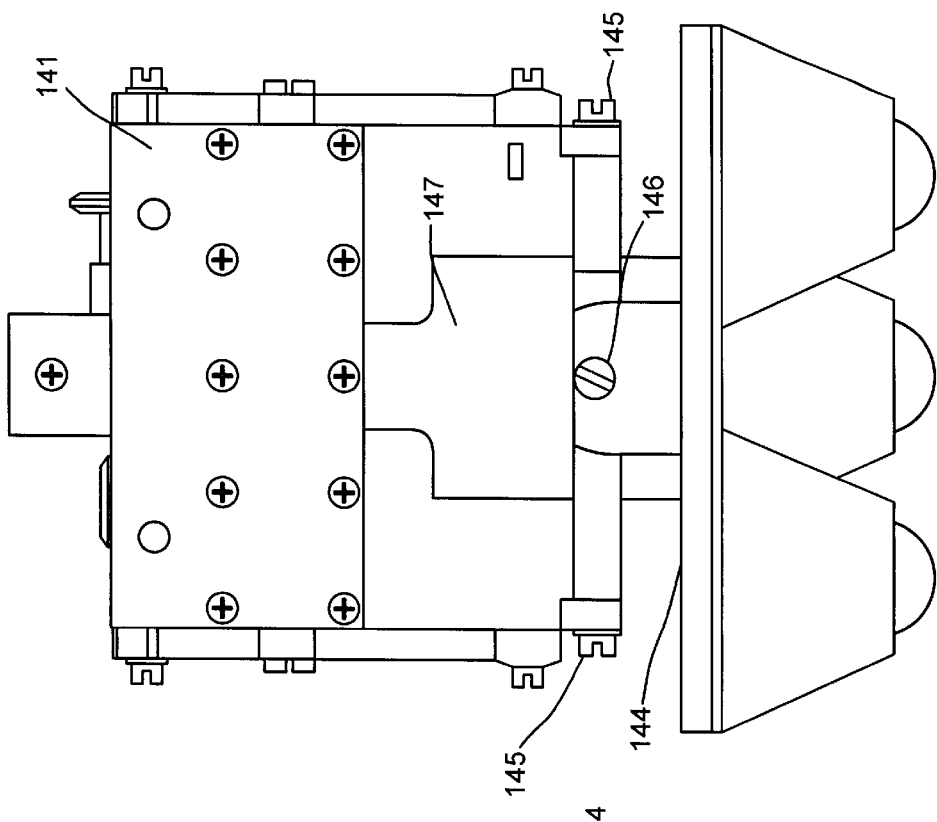
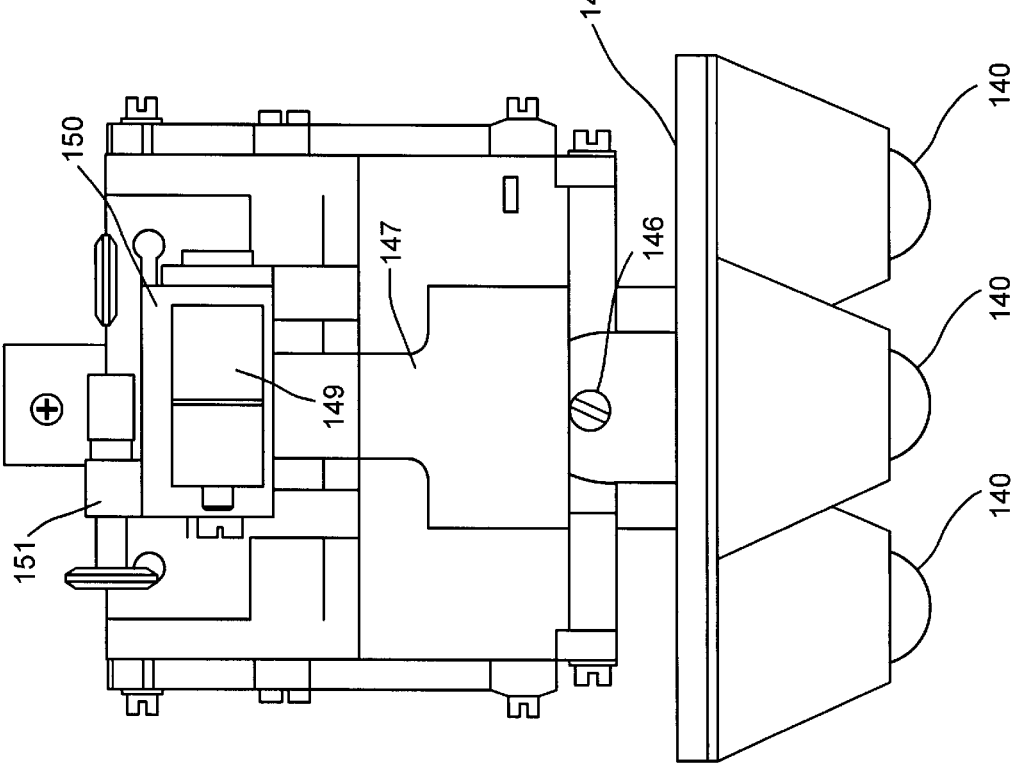

REPORT GENERATION

METHOD AND APPARATUS FOR INSPECTING A SUBMERGED STRUCTURE

This application claims benefit of provisional No. 60/066,212 filed Nov. 20,1997.

TECHNICAL FIELD

The present invention relates to an underwater apparatus, system and method for inspecting and determining the condition of a submerged structure whether it be a ship, drilling rig or any other underwater structure. Whether it be a regular routine inspection, or an inspection occasioned by an accident at sea, which may raise concerns respecting the structural integrity of the structure. The apparatus is particularly suited to inspect the hull of a ship without submitting the same to a costly dry dock procedure. The present invention does not require the ship to be docked, as it is highly portable and can be deployed in any appropriate body of water. Moreover, the exact position of the hull being inspected is also determined. Accordingly, the size and location of any irregularities and/or defects in the hull of the ship or the coatings that protect it are determined to a tolerance of a few centimeters.

BACKGROUND

Cost-efficient operation of a sea-going vessel, whether it be a tanker, a container ship, a floating production platform, or a cruiser, demands rigorous monitoring of the integrity of the hull. When referring to the integrity of the hull, it is important to note that this means much more than the ability of the structure to withstand the application of normal operating stresses. More particularly, in addition to the continuous relatively mild stresses applied to a vessel at rest in port, or at sea, vessels must also be able to withstand the sometimes every violent forces experienced by ships at sea during storm and other less than ideal conditions, whether they be waves, wind, or combinations of the same.

Key to the maintenance of the structural integrity of a ship is protection of the surface of the steel hull from the corrosive effects of sea water. As is well known, the salinity of sea water causes it to chemically attack the surface of a ship.

More particularly, and by way of example, the heavy salt content of ocean water will tend to eat away at the material of which metal vessel hulls are made. The result will initially be minor pitting, which tends to be localized on account of the configuration of the ship's hull, the materials of which the hull are made, joints between various components of the hull, and other factors. Eventually, such corrosion will compromise the overall integrity of the ship under normal operating conditions and, of course, could have catastrophic effects in the event of inclement weather or a collision with debris, another vessel, or on account of being run aground.

Even fiberglass vessels must be coated to be protected from other deteriorating elements in the sea, such as the build-up of organic materials, marine organisms such as barnacles, and the like.

Thus, the first line of defense is the protection of the hull of a ship with an appropriate coating. Such coatings are selected for their properties of long life in sea water, resistance to radiation, ability to discourage the growth of marine life on the surface of the hull of the ship, adhesion and general toughness, among others. Likewise, a crucial element of the survey of a ship, is the inspection of the coating, which is often the first element in the ship to indicate the onset of a problem in the overwhelming majority of situations.

For these reasons, the issuing and renewal of certificates of seaworthiness for ships is dependent upon a rigorous inspection of the hull of the ship in which certain characteristics are checked throughout the entire hull. In particular, the condition of the hull is checked for corrosion and/or irregularities. The nature and amplitude of any observable dents in the surface of the hull is also examined.

Generally, these inspections are carried out in dry dock. The experts of the official bodies authorized to carry out these inspections meticulously inspect, square meter by square meter, the hulls of ships which are submitted for inspection.

Putting a ship into dry dock is a very time consuming and expensive task to perform and results in greatly increasing the cost of maintaining a ship. This cost is particularly large in the case of a large container ship where each day out of service costs the owner tens of thousands of dollars, or in the case of floating production platforms, where the cost due to lost production can be orders of magnitude higher.

The disadvantages of this process are compounded in the case of high-tonnage ships, whether these be, for example, oil tankers, ore carriers or container ships, because the sizes of dry docks are becoming less and less able to accommodate the growing size of such ships, because the large commercial ports with a dry docks that are capable of accepting the ships are ill-equipped, and because of the actual cost of taking the ships out of service.

As a result of these problems, there has been proposed a process involving the installation of an apparatus incorporating a transceiver-carrying transport device or carriage which is capable of moving underwater over the surface to be inspected. In particular, the system described in the background of U.S. Pat. No. 4,308,600 contemplates a carriage which is capable of moving on the surface of the submerged structure to be inspected. The carriage carries a transducer, for example a television camera, which is connected in a closed circuit to a receiver located on the surface. The receiver is suitable for producing an image of the surface which the carriage is scanning.

In principle, such a system is intended to carry out, from a location on land, the multiple checks to which the hull of a ship must be subjected. Most importantly, it is intended to do this while the ship is afloat, thus avoiding the costs associated with submitting the ship to a costly dry dock procedure.

However, the inspection carried out in accordance with this system suffers because the position of the carriage or operating apparatus used on the surface over which it is moving cannot be determined very exactly at any instant. This information is of value, for example, in order to make it possible to make a comparison between deterioration measurements made by transceivers carried by the apparatus, during successive statutory surveys. Thus, dry dock surveys of hull condition remain the standard.

However, as alluded to above, present world facilities simply cannot accommodate the number of ships which need to be inspected. Accordingly, there are numerous vessels on the sea today which are far behind their inspection schedules. As is apparent, the same poses the possibility of many problems, some of potentially devastating magnitude.

More particularly, in addition to the cost attendant to the mechanically inefficient operation of a vessel, failure to perform maintenance on a preventative basis will, sometimes, have a dramatic impact on the cost of a repair. This is because of the fact that if a small problem is left unattended, continued corrosion will cause it to become a serious problem. Repair costs will be far in excess of the cost of a repair made when deterioration is just beginning to occur. More seriously, however, if the problem is left unattended, it may result in weakening the structure of the vessel to the point that the application of relatively routine forces will cause the structure to break down, not only again increasing the cost of repair, but also posing the potential for loss of the vessel and, far worse, environmental disaster.

As a consequence of the above problems, including the expense of conventional dry dock inspection procedures, attempts are being made to overcome the disadvantages of present submerged vessel inspection systems and processes. In this regard, the assignee of this application has proposed that the high resolution acoustic positioning systems developed by the assignee be employed in an underwater inspection.

Patent Cooperation Treaty International Application No. P. C. T./N 094/00060 discloses a diver delivered unit which may be operated directly by a diver or otherwise in a measurement area marked by a plurality of lights. The unit is delivered to the area of the hull of a ship afloat in a harbor by a diver. In accordance with the preferred embodiment described in this application, the unit is moved over the hull of the ship by a diver, although the possibility of moving the unit on the surface of the hull without a diver is vaguely alluded to. While this disclosure is somewhat general, it appears to suggest that magnets may be used to adhere the unit to the hull of a ship while the unit is being propelled along the surface of the ship by thrusters.

As alluded to above, the above Treaty filing suffers from the disadvantage of being dependent upon diver delivery. Moreover, the use of a plurality of lights to guide the system is an additional task with its own attendant cost and calibration problems. The use of magnetic wheels, if that is what is meant, would appear to present problems on account of surface contours, loss of engagement, and other factors. In particular, if there is a loss of engagement, it is likely that the gap created by the same will exceed the distance over which the magnets will operate to restore contact.

SUMMARY OF THE INVENTION

The invention, as claimed, is intended to provide a remedy. It solves the problem of how to provide a reliable, economical and consistent way of inspecting the hull of a ship without resorting to the costly procedure of dry docking the ship.

Moreover, there are additional problems which the systems, described in the above background, do not even attempt to address. Even if the components which form the hull of the ship are in good condition, there may be other problems which, in time, may cause a hull to fail. For example, if a vessel is subjected to a large force, for example by being run aground, the shape of the overall hull may be distorted. Accordingly, the profile of the hull moving through the water may not be symmetrical and may result in the concentration of forces of unusual and unanticipated magnitude at particular point or points. This could, in time, have the effect of causing a serious failure at that point or points. Thus, examination of the overall shape of a vessel, provided in accordance with the present invention, will yield useful information about the condition of the ship. Such information comes as a cost free bonus in accordance with the method of the present invention.

As will be described below, in accordance with the preferred embodiment of the invention, the above disadvantages of the systems in the literature are addressed. More particularly, the system of the present invention comprises a remotely operated vehicle (ROV) which can be introduced into the waters of a port from a position on the land (or even at or close to the site of an accident possibly far at sea). The ROV is equipped with inspection cameras, position sensing equipment and non-destructive test equipment adapted to inspect and measure the characteristics of the submerged hull to be inspected. The non-destructive test equipment provides measurement of key vessel parameters, including plate thickness, plate pitting, plate delamination, plate fracture, coating thickness, and cathodic protection device potential. An integrated data set, comprised of all measurements correlated in time and hull position, is generated and recorded at a controlled spatial resolution on the hull. The ROV is adapted to propel itself toward and over the surface of the submerged hull of the ship, being guided by either a human operator who steers the ROV from the control console (which may be on land or on the ship being inspected) using an on board camera and acoustic navigation system, or guided automatically by a computer which is programmed to execute a stored inspection sequence over the submerged hull. In accordance with the preferred embodiment, the position of the ROV on the hull provided by the acoustic navigation system may be initially determined by the placement of three or more electro-acoustic position transducers at known points on the hull of the ship. It is also possible in accordance with the present invention, to steer the ROV over the entire vessel, and then to process the electro-acoustic position information to create a database which comprises the shape of the vessel. This information can then be used both to create inspection results "maps" and to generate automatic scan plans of the submerged portion of the hull for subsequent inspections.

It is also contemplated that in accordance with the invention, after an initial survey of the full ship hull, areas which are suspect can be subjected to a slower more detailed and/or more comprehensive inspection at finer spatial resolution, and possibly with different NDT instrument settings optimized for the local conditions.

ROV adhesion to the surface of the submerged hull is achieved by employing a Bernoulli effect for steady state, incompressible flow across an orifice. By flowing water across an orifice formed at the interface of one or more dedicated suction zone(s) and the hull surface under and around the suction zone, a pressure drop is created in the direction of water flow. The reduced pressure within the suction zone(s) develops a suction force proportional to the product of pressure drop and suction zone area. The suction force is largely normal to the hull at the suction zone, and in a direction which results in the suction device adhering to the hull. The interface of the suction zone and the hull is formed using a compliant skirt which provides good conformance to rough, uneven or undulating hull surfaces, while generating minimal drag and compression forces during ROV motion.

It is also noted that in accordance with the present invention, movement of the ROV along the surface of the hull of the ship is achieved through a combination of thruster power and wheeled propulsion. The result is the positive control of position by virtue of the contacting drive wheels and drive augmentation provided by the thrusters whose thrust assists the wheeled propulsion, both in direction and magnitude. The thrusters and the driven wheels can share a common power plant, with the drive wheels driven directly by the propulsion thruster motors via mechanical connection.

BRIEF DESCRIPTION OF THE DRAWINGS

One way of carrying out the invention is described in detail below with reference to drawings which illustrate a specific embodiment of the invention:

FIG. 9 is a detailed view of the right thruster of the inventive ROV along lines 9—9 of FIG. 8;

FIG. 10 is a detailed view of the thruster of FIG. 9 inventive ROV along lines 10—10 of FIG. 9;

FIG. 15A is a side elevational view of the inventive NDT sled along lines 15A—15A of FIG. 14;

FIG. 15B is a side elevational view of the inventive NDT sled along lines 15B—15B of FIG. 14;

The inventive method and apparatus will be described with respect to a ship hull inspection, with the understanding that the present inventive method and apparatus may also be used to inspect oil rigs and other submerged structures.

DETAILED DESCRIPTION OF THE PREFERRED EMBODIMENTS

Figure 1:
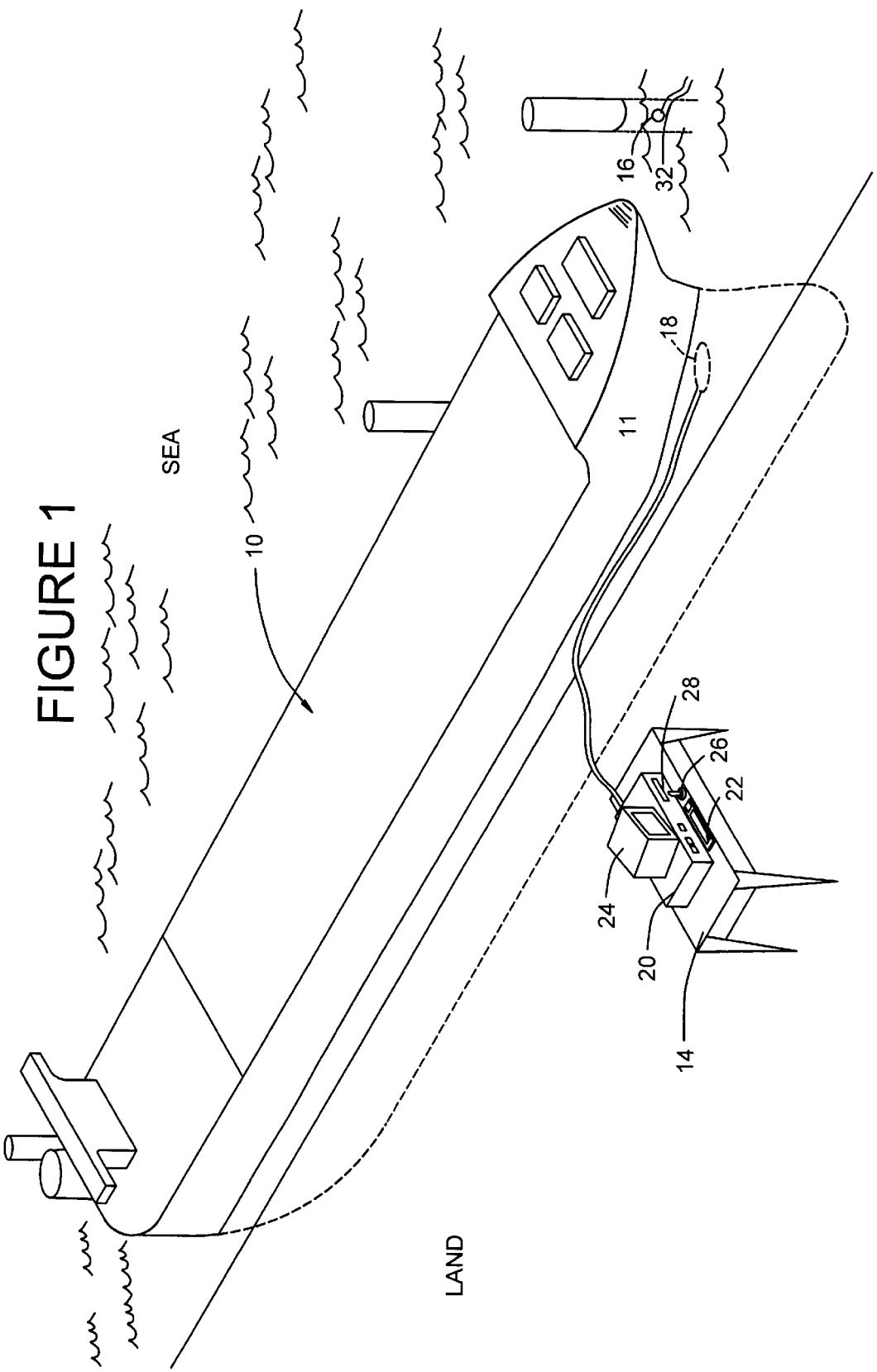
FIG. 1 is a perspective view of a ship docked at a facility equipped with the apparatus of present invention.

Referring to FIG. 1, a ship 10 having a hull 11 or any other submerged structure requiring periodic inspection such as a dam, may be equipped with an inspection system 12 constructed in accordance with the present invention. Inspection system 12 comprises a topside computer controlled operator interface console 14, a plurality of underwater transceivers 16 and a remotely operated vehicle (ROV) or robot, which functions as ROV 18. The underwater transceivers 16 are preferably mounted directly to the hull using one or more methods, however, the transceivers may also be mounted to fixed land based features (sea bed, pier pilings, etc.). In the latter case, it is also necessary to know the position of the ship with respect to the fixed transceiver network comprising transceivers 16. In this case, it is necessary that a number of transceivers 19 sufficient to completely define the position of the ship be used. Such transceivers 19 should be secured to the hull 11 of the ship, and, in accordance with the present invention, are secured at minimum three points. See FIGS. 2 and 3.

Generally, the inventive system can operate under the control of a human operator at console 14. Console 14 includes a computer network 20 (sometimes referred to herein as the "computer"), a keyboard 22, an appropriate monitor 24 and an analog input device such as a joystick 26. The system also includes a number of mass data storage units (magnetic disk drives, magneto-optical drives, etc) 28 which may be used for program and data storage and exchange.

Power to the system is provided by the power mains, which may be derived from shipboard power, pier-side power, or stand-alone generator sources. The power mains provide power for the integrated system, including topside controls, the underwater ROV, and acoustic transceivers. The underwater ROV 18 is powered through an electrical cable (tether) 30. Likewise, transceivers 16 and 19 are also powered by appropriate electrical cables 32 connecting the transceivers to the topside control consoles 14. In addition to carrying power, tether 30 and cables 32 also carry information, control and associated signals, as will be set forth in detail below.

Underwater ROVs, which are capable of movement underwater are known. Likewise, the systems for controlling thrusters on board such ROVs to achieve desired movement of the ROVs are also known in the art. Such ROVs incorporating such control systems are sold, for example, by the assignee of the present application. Such underwater vehicles may be modified in accordance with the teachings of the present specification and be employed in the system of the present invention to carry navigation equipment and appropriate inspection devices.

Figure 3:
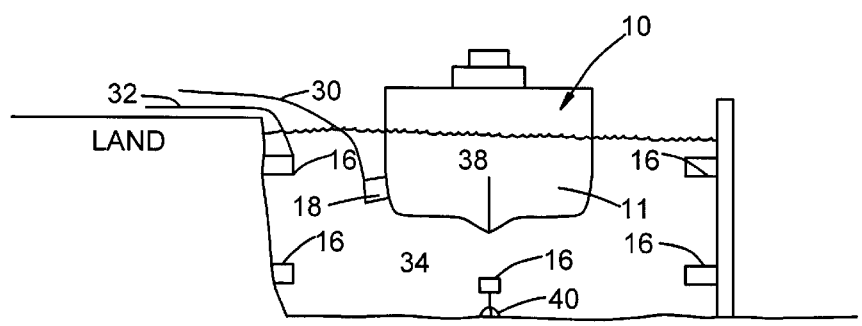
FIG. 3 is a cross-sectional view of a ship being inspected with the present invention along lines 3—3 of FIG. 2.

As can be seen most clearly in FIG. 3, transceivers 16 are positioned underwater at a plurality of points which are selected to provide acoustic line-of sight communication for the emission of an acoustic signal from every point on the submerged hull 11 of the ship to transceivers 16. In accordance with the invention, a sufficient number of transceivers 16 are placed so that this can be achieved with respect to at least three, and preferably more of the transceivers 16 from any point on the submerged hull.

More particularly, the hull of a ship 10, submerged in water 34, is surveyed by ROV 18 in accordance with the present invention. One or more acoustic pingers 38 on ROV 18 receives a signal from the console 14, which causes it to emit an acoustic signal, which is received by transceiver 16. The distance between the transceiver 16 and the pingers on ROV 18 can then be calculated by computer network 20 based upon a calibrated speed of sound in the water and the acoustic travel time, i.e., the time between the emitted acoustic pulse at the pinger and the received pulse at the transceiver. Once the position of the pingers on the ROV are known, it is possible to calculate the position and orientation of ROV 18, and further, because the position of each inspection device on the ROV is also known with respect to the ROV frame of reference, it is also possible to know the exact position of each inspection device and, accordingly, the specific points on the hull 11 under inspection.

A high accuracy sonic (acoustic) navigation and positioning system of the type sold under the trade name SNAP by the assignee of this application and specifically designed for precise underwater tracking of underwater ROVs and providing data at high update rates in high multipath environments is employed in the system of the present invention. At 100 meters, ROV pinger to transceiver range (distance) errors are less than 2 cm, repeatability is better than 0.5 cm., and sampling rates up to 10 Hz can be achieved with such prior art systems. Such high accuracy navigation systems are adaptable for use in rivers, lakes, ponds, or the open ocean, but are exceptionally well-suited to high multipath environments such as harbors, enclosed tanks, dams or tunnels, under ice cover, beneath ships, and around submerged structures.

Such high accuracy navigation systems are based on a set of compact and durable acoustic transceivers 16 in the water around ship 10, transceivers 19 on ship 10, and pingers 38 on ROV 18, each independently capable of transmitting and receiving high-frequency acoustic pulses. A computer network 20 controls the acoustic network of transceivers and is used for data acquisition, and for the processing, display, and output of position data. Each transceiver is connected to the system controller through a twinaxial cable 32 which provides power and a data transfer path, as shown FIG. 1. In a typical application at least three transceivers 16 are deployed to form a stationary baseline array and one or more, but preferably three, hull mounted transceivers 19 are tracked by the stationary baseline array.

Each transceiver in this high accuracy navigation system is independently controlled to transmit or receive acoustic pulses with an approximately hyper-hemispherical beam pattern. The transceivers are mounted in rugged, cylindrical, stainless steel, sealed pressure cases which allow easy deployment in a wide variety of applications.

The high accuracy of the navigation system is due to the use of broadband high frequency acoustic pulses centered at 300 kHz. As noted above, operating at the maximum range of 100 meters the range data is accurate to within at least +/−2 cm, and repeatable to within 0.5 cm. In order to obtain the accuracy stated above, speed of sound errors must be limited to 1 cm at 100 meters or 1 part per 10,000. Repeatability is not affected by sound speed errors, but will be affected by variations in the speed of sound over a period of hours or days.

This high accuracy navigation system is ordinarily operated in a "long baseline" mode. Other types of typical long baseline systems operate at much lower frequencies and consist of an array of transponders covering an area of 1,000 to 10,000 square meters. The 'baseline' transponders are usually securely positioned on the sea floor using tripods, or allowed to float above the sea floor on moorings. System accuracy is dependent upon knowledge of these baselines, and unobstructed line-of-sight is required between the baseline transponders and the target to be positioned. There are two main differences between typical long baseline systems and the high accuracy sonic navigation system of the type used in the present invention. The use of high frequency signals limits the range (100 meters, typical at 300 kHz) and each of the baseline array elements is hard-wired to the computer.

In order to maintain the distinction between the cabled elements of the high accuracy navigation system arrays of the type used in the present invention and the "wireless" elements of an ordinary long baseline system, we refer herein to the high accuracy acoustic devices of the type employed in the present invention as "transceivers" rather than transponders. A wired baseline array forms a network of transceivers which can be referred to as a "net", and the individual transceivers can be considered as "net elements".

To obtain a position fix, the high accuracy navigation system first commands the target pinger 38 to transmit a pulse. This pulse is received by the three (or more) network transceivers 16, and the one-way travel times are determined. Using the estimated sound speed, these travel times are converted to slant ranges (distances). The slant ranges are then converted to the Cartesian (x,y,z) positions by knowledge of the geometry of the net elements. The computed position and orientation of the array can be adjusted during calibration so that these x,y,z positions are reported in a global coordinate system or one which is referenced with respect to some important features of the ship's hull 11.

The pingers 38 are the sonic devices which the high accuracy navigation system uses to determine relative range and position of ROV 18. Transceivers 19 are used to determine ship position. Transceivers 16 form the stationary array to which all ranges, from both ROV pingers 38 and hull-mounted transceivers 19, are measured. All the transceivers are interchangeable, as each can transmit and receive acoustic signals. Thus, any of the transceivers may be used in the baseline array of transceivers 16 fixed with respect to the sea floor.

The transceivers are connected to the twinaxial subsea cable 32 consisting of a 100 meter subsea twinaxial cable and a five meter deck cable. Longer subsea cable and deck cable lengths may also be employed. The deck unit provides the connection between the cable 32 and host computer network 20.

A depth sensor may also be used to measure the depths of the transceivers in the baseline array so that the coordinate system can be adjusted to be level. It can also be used during tracking as a substitute for the high accuracy navigation system acoustic indicated depth or as an input to a filter which combines the two depth measurements to obtain an improved depth estimate.

A tripod 40 (FIG. 3) may be used to mount the baseline transceiver in applications requiring seabed installation. Telescoping legs allow stable installation in a rocky seabed, and a rotating and tilting mount supports aiming of the transceiver tip so as to optimize signal reception. Custom tripods or mounting fixtures can be designed for other applications.

Figure 4:
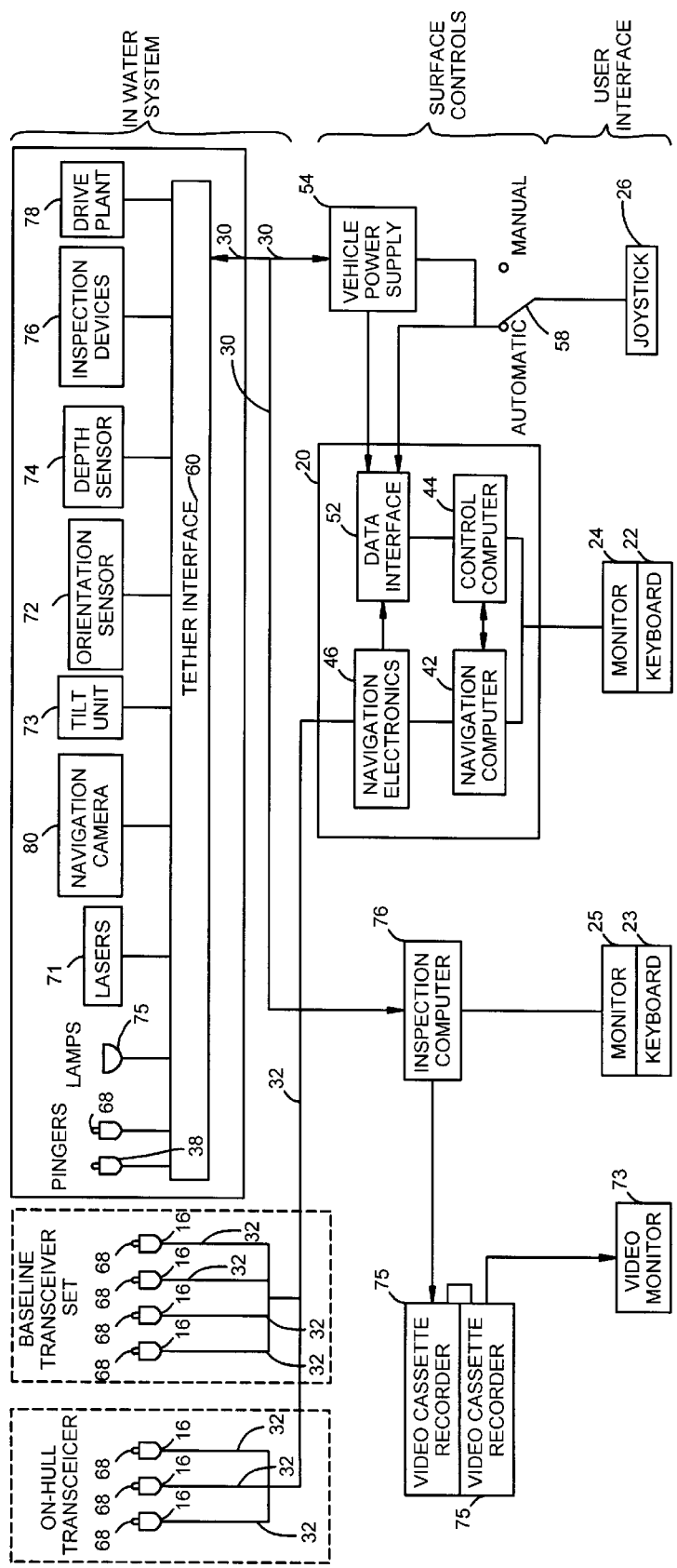
FIG. 4 is a schematic diagram of a position detecting system employed in the present invention.

A more detailed understanding of the operation of the present invention may be achieved with reference to FIG. 4. Generally, the inventive system 12 comprises a computer network 20. Computer network 20 includes one or more computers for ROV navigation and ROV control (including position control). In the embodiment illustrated in FIG. 4, the ROV navigation and control functions are provided by two computers, the navigation computer 42 and a ROV position control computer 44. In a configuration consisting of a single computer, these two functions, navigation and control, would be operating as two separate processes, or threads, within that computer.

Navigation computer 42 interfaces with appropriate navigation electronics contained on a board 46 adapted to send ROV pinger target position information to computer 42 and receive control signals from computer 42. Navigation electronics 46 are also coupled to the in-water navigation electronic systems associated with ROV 18. Coupling of in-water systems associated with ROV 18 to navigation electronics 46 is achieved using tether 30, as is illustrated in FIG. 4, which illustrates the principal elements of the electronic system, and the paths and directions used by information and drive signals during operation of the system.

Console 20 also includes digital data interface boards 52 which are coupled to an ROV position control computer 44. Likewise, boards 52 are coupled to vehicle control signal lines which connect to the ROV 18 over tether 30, via the vehicle power supply 54. Information may be input into computer 44 through boards 52 by a joystick 26 whose output is switched by a switch 58 to either boards 52 or is connected directly to vehicle controls via the power supply 54. This switch 58 provides a method for the operator to control the vehicle manually without computer intervention, or the control computer 44 is capable of operating the vehicle in automatic mode, wherein the ROV is driven under software control through a course which is dynamically programmed. This course is determined by a series of waypoints determined by the operator, and the software controls the ROV to drive a track line, or trajectory, from one waypoint to the next.

Vehicle power supply 54 outputs an electrical power signal which is coupled by tether 30 to the ROV 18. This electrical power signal provides the power to operate the ROV 18, including power for its vehicle movement systems, its inspection systems, and its position sensing systems.

Interface between the operator and the console is provided by a monitor 24 and a keyboard 22. A single monitor and keyboard can service the navigation computer 42 and a ROV position control computer 44.

The in-water systems include ROV 18 and the on-board propulsion, navigation and inspection systems. More particularly, the ROV 18 carries appropriate inspection and navigation instrumentation, including inspection devices 70, an orientation sensor 72 and a depth sensor 74. The output of inspection devices 70 is communicated by tether 30 to an inspection computer 76 which is coupled to dedicated monitor 25 and keyboard 23. Output from ROV navigation devices and all other on-board devices is communicated via the tether interface 60 and tether 30 to ROV position control computer 44. The ROV 18 also incorporates two or more pingers 38, each of which includes a transducer 68. A navigation camera 80 is also coupled to tether interface 60. The navigation camera 80 function is augmented by an electrically controllable tilt unit 73, illumination lamps 75 and with laser projectors 71. The tilt unit can point the camera and lasers through an angular arc of 180 degrees. The lasers are mounted to either side of the navigation camera, precisely aligned to the axis of the camera, to provide a visual measurement reference within the field of view of the camera image. The in-water systems for ROV 18 are completed by a drive plant 78, which provides the motive power for movement of ROV 18.

As has been noted above, the function of the navigation system illustrated in FIG. 4 is to determine the position of the ROV 18 by determination of the positions of ROV mounted pingers 38. Because the shape of the hull 11 in most small areas is relatively flat, and the configuration of the ROV 18 is known together with the position of pingers 38 on ROV 18, this determination of the position of pingers 38 at a large number of locations of ROV 18 on the hull 11 of ship 10 will provide the location of a large number of points on the hull 11 and thus the three dimensional shape of the hull 11.

Likewise, for each of these points, measurements of hull 11 plate thickness, coating thickness, cathodic protection device potential and other measurements taken on the surface of the hull 11 of the ship may be associated with these points in alphanumeric printouts (reports), topographical maps, and other 2-D and 3-D visualization methods illustrating and documenting the condition of the ship. Such images may be enlarged and rotated in space, as required to provide the desired degree of specificity for examination of a particular condition on a particular ship.

Transceivers 16 each are comprised of a transducer 68 which can both transmit and receive. Transducers 68 on transceivers 16 or transceivers 19, when driven by an appropriate electrical signal, will emit an acoustic signal. Transducers 68, also on transceivers 16 and transceivers 19, when excited by an acoustic signal will output an electrical signal to board 46. The signals received and transmitted by transceivers 16 and 19 are connected via cables 32 to navigation electronics 46.

Generally, the determination of position information begins with pulses output by acoustic transducer 68 on ROV mounted pingers 38. The signals which drive pingers 38 are sent over tether cable 30 from the navigation electronics 46 which generates those signals.

In accordance with the preferred embodiment of the invention, transceivers 16 and 19, and pingers 38 all operate at the same acoustic frequency. Such operation, beginning with the determination of the ship's position relative to the fixed transceiver net, includes the stimulation of one of the fixed transceivers 19 to cause its transducer 68 to emit an acoustic pulse at the desired acoustic frequency. This pulse is received by all of the net transceivers 16. Each transceiver 16 will then signal the decoding circuitry in the navigation electronics 46 that it has received an acoustic pulse. The time between the emission of the pulse from the particular transceiver 19 and its reception of that pulse at each of the transceivers 16 gives the distance between all transceivers 16 and the particular transceiver 19.

Using the well-known principle of triangulation, the position of the particular transceiver 19 in space may then be determined. In principle, it is not necessary ranges to more than three transceivers 16, but using four or more ranges does afford the opportunity to obtain redundant information and check for errors or improve accuracy and repeatability.

Once the position of the first of the transceivers 19 is known, the above process can be repeated for a second of the transceivers 19. The process is also repeated again for a third of the transceivers 19. Knowing the position of the three transceivers 19 attached to the hull 11, provides a unique determination of the position and orientation of the hull with respect to the fixed transceiver net 16.

In similar fashion, transceivers 16 are used to determine the position of each of the pingers 38 on ROV 18, and thus determine the position of the ROV and the corresponding points 77 (FIG. 8) on hull 11 being inspected and measured. This is done by each of the pingers 38 sending an acoustic pulse to all of the transceivers 16, and then repeating the process for each of the remaining pingers 38 on ROV 18, using triangulation to determine the position of each of the pingers 38. Computer 46 then computes the position of the measurement instrumentation on ROV 18 using the same triangulation techniques it uses to determine the position of transceivers 19 and hull 11. Since the position of the hull 11 is known, and its shape is known, the position of the instrumentation inspection points 77 on the hull 11 of the ship may be determined.

At that point, the positions of each of the transceivers 19 is known. The position and orientation of the ship is also known, and data collected over the cable during or about the time of the position determination operation can be associated with a particular point 77 on the hull 11.

The above operations are performed through the use of the navigation electronics board 46 which sends information to the navigation computer 42, which in turn calculates the position of the various targets. The corresponding position information, in x,y,z Cartesian form is sent to the ROV position control computer 44. In automatic mode, computer 44 sends drive control information to the drive plant on the ROV 18 via the tether 30. The computer software calculates the appropriate drive control values by comparing the current position and orientation of the ROV to the desired position and orientation and computing drive values which cause the measured difference, or position state error, to be minimized. In manual mode, the operator performs this function by monitoring the ROV position and driving it by use of the joystick 26.

Figure 5:
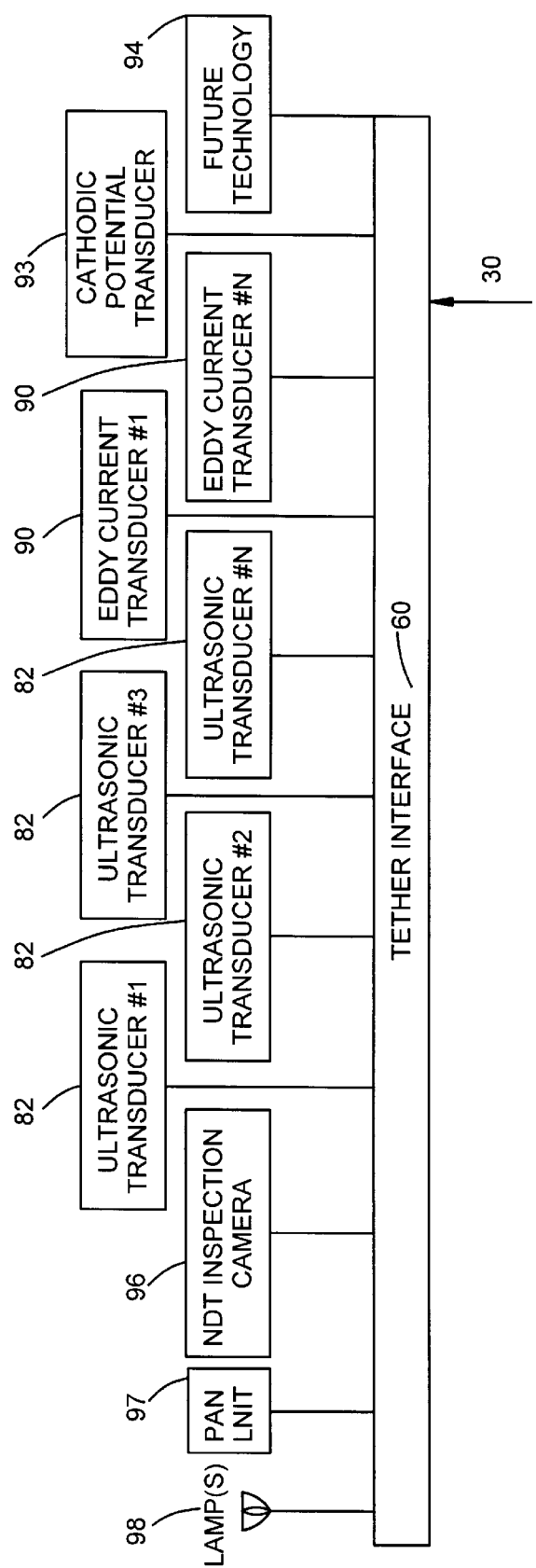
FIG. 5 is a schematic diagram illustrating the electronic inspection system carried by a ROV inspection device constructed in accordance with the present invention.

The details of the inspection devices attached to the ROV 18 are illustrated in FIG. 5. On board inspection devices include one or more each of ultrasonic test (UT) measurement systems, eddy current test (ET) measurement systems, potential field measurement systems, and video inspection systems. Other measurement technologies may also be employed in similar fashion.

The ultrasonic measurement system employs one or more non-contact, water path coupled transducers 82. When employing multiple transducers, the devices can be configured to operate at different water path distances, ultrasonic frequencies, focus characteristics, and orientations relative to the local hull surface to optimize the transducer performance for a specific desired measurement. Moreover, the electrical characteristics of the signals which drive the transducers 82 may be varied over time to achieve a wide range of functions g from a single transducer. Some of the transducers 82 may generally comprise an ultrasonic emitter and an ultrasonic receiver for, respectively, emitting a test signal and receiving the reflected measurement signal.

The eddy current measurement system may include one or more eddy current transducers 90. Potential measurement system includes one or more transducers 93 for cathodic protection device potential measurement, as well as other measurement devices 94.

Finally, the system also carries an inspection camera 96 which enables visual inspection of the hull 11 of the ship 10. Camera 96 also includes appropriate controls for varying the nature of the visual inspection. More particularly, camera 96 is of the type which has electrically controllable camera pan 97, electrically variable zoom functions and electrically controllable focusing. Operation of camera 96 can also be enhanced by provision of inspection lighting 98.

Figure 6:
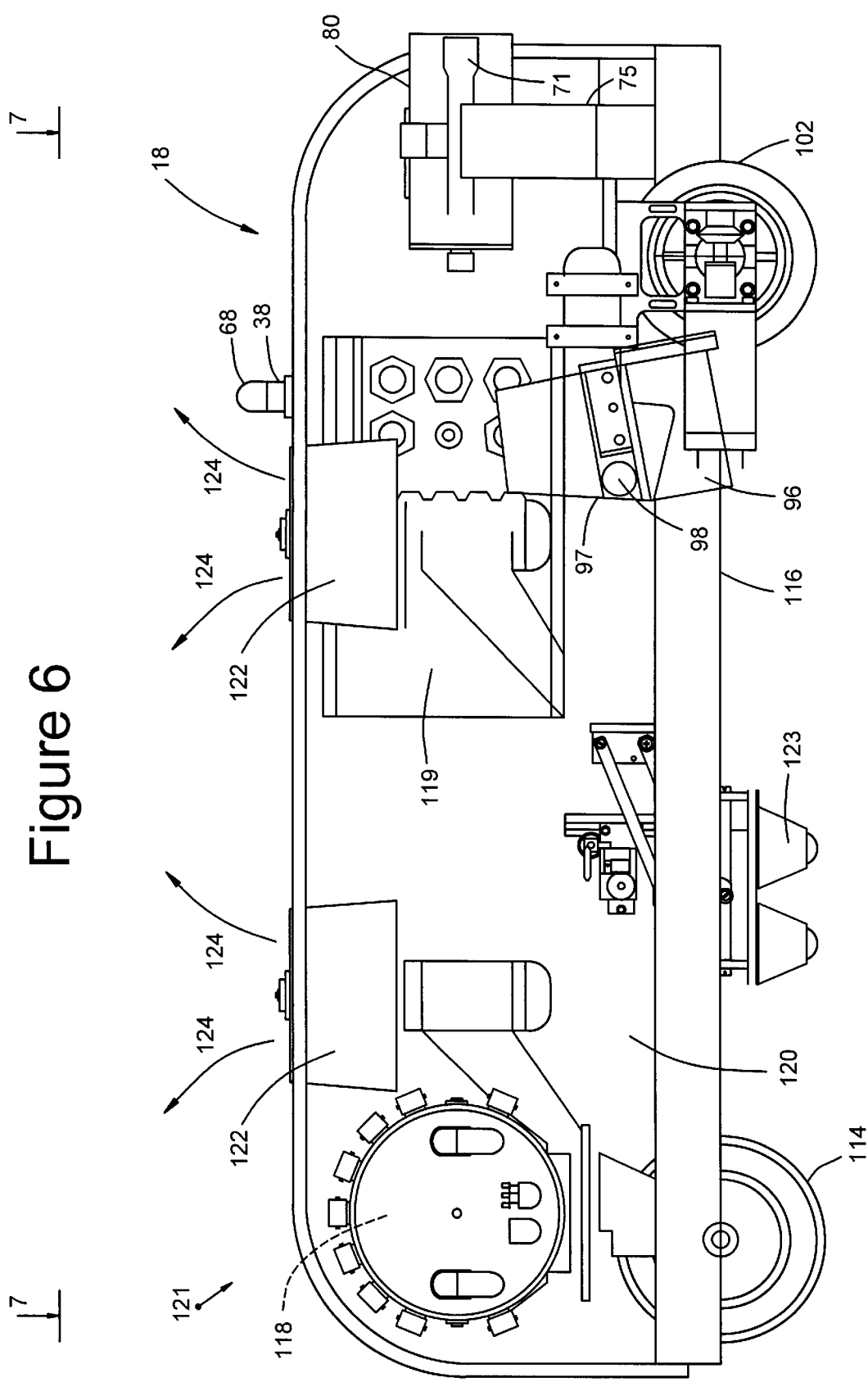
FIG. 6 is an elevational view of the ROV of present invention.
Figure 7:
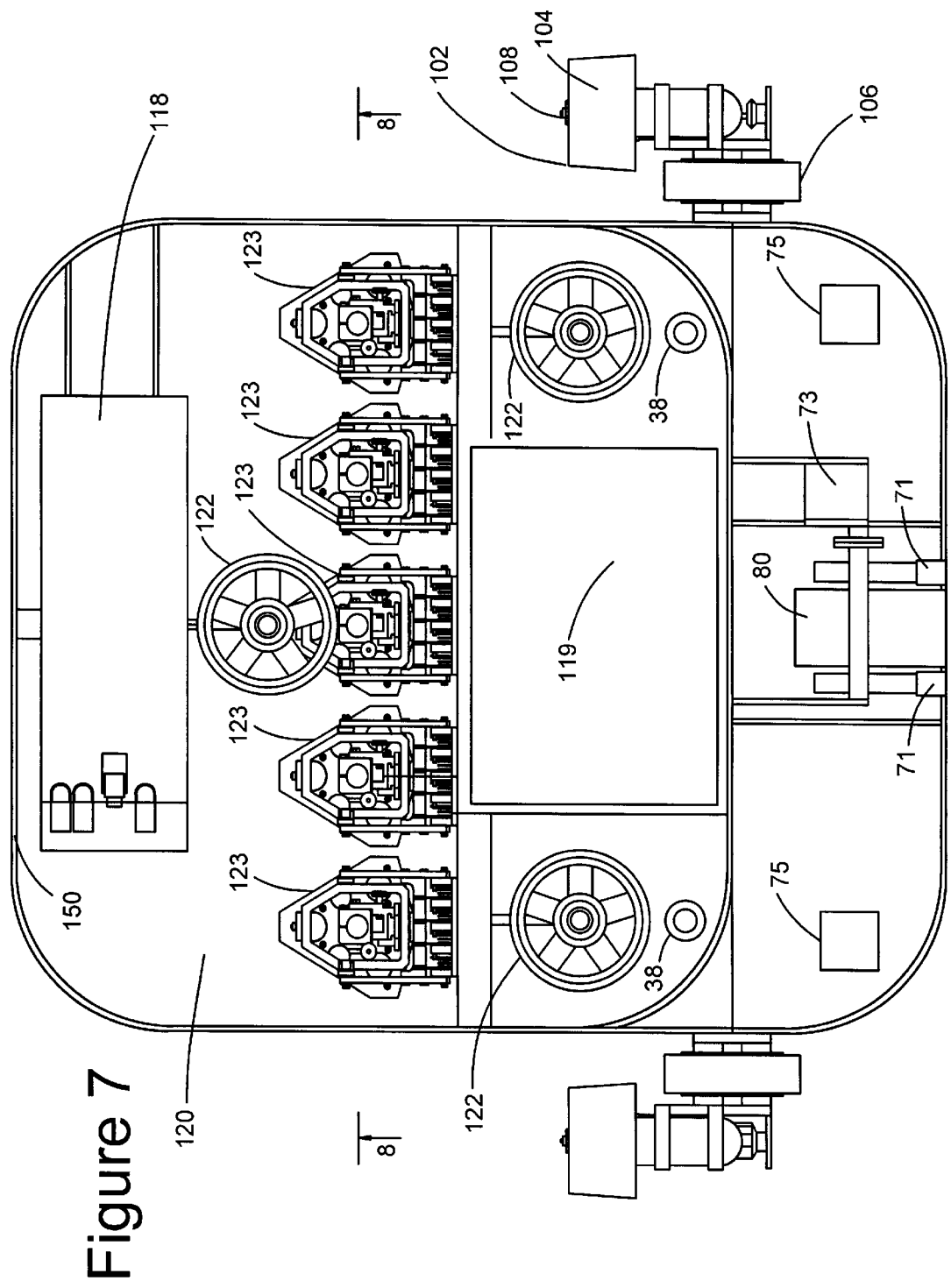
FIG. 7 is a plan view of the inventive ROV along lines 7—7 of FIG. 6.
Figure 8:
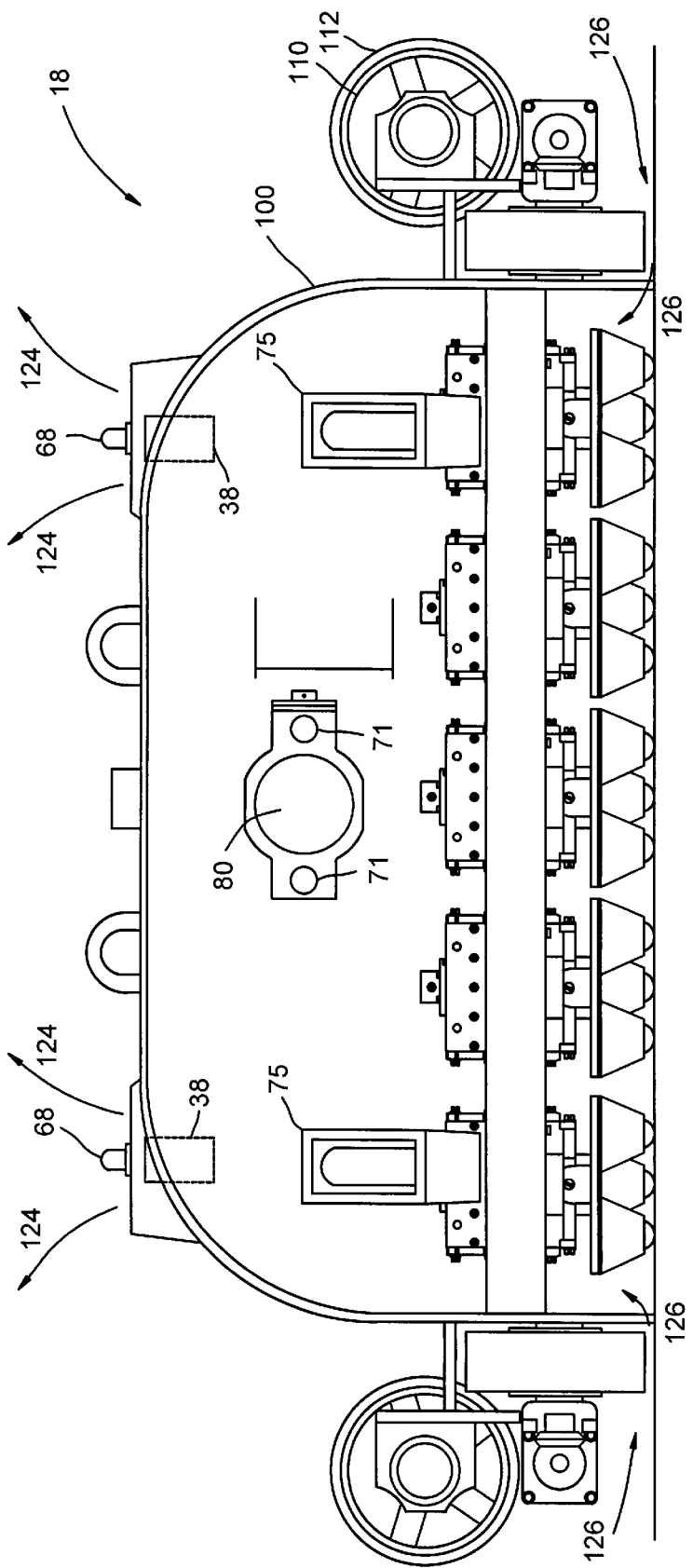
FIG. 8 is a side elevational view of the inventive ROV along lines 8—8 of FIG. 7.
Figure 11:
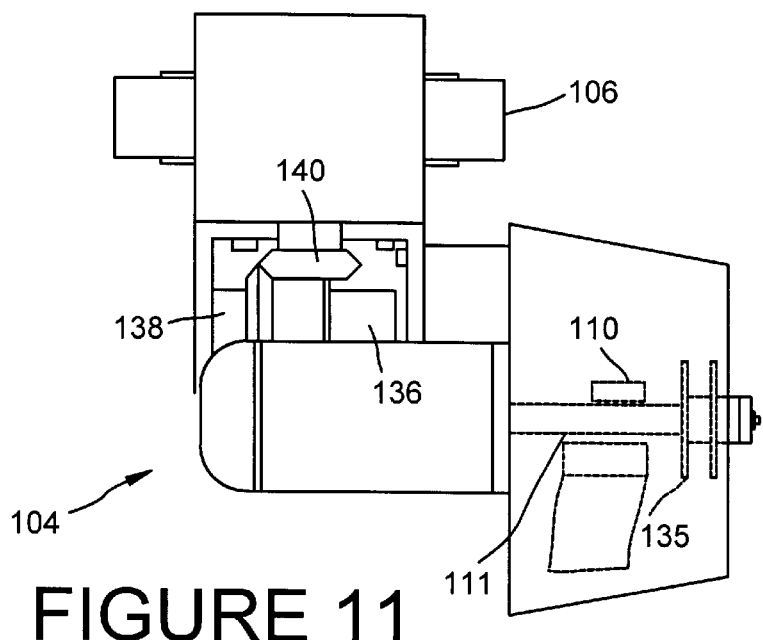
FIG. 11 is a detailed view of the thruster of FIG. 9 inventive ROV along lines 11—11 of FIG. 10.
Figure 12:
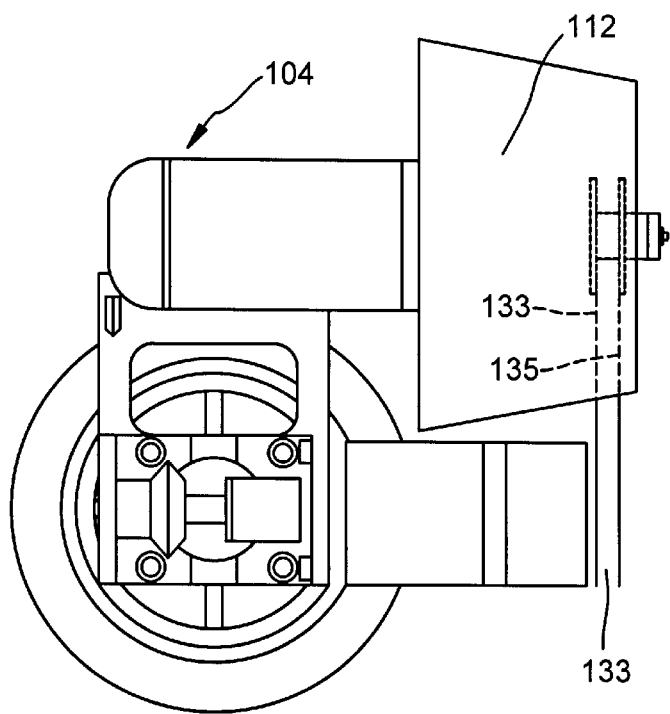
FIG. 12 is a detailed view of the thruster of FIG. 9 inventive ROV along lines 12—12 of FIG. 9.

Referring to FIGS. 6 through 8, the construction of ROV 18 is illustrated. ROV 18 comprises an outer body 100 which functions as a protective housing for the ROV internal components, and as the pressure boundary between the internal suction plenum 120 and external ambient pressure 121. The frame member 116 includes mounting provisions for the internal components and the outer body 100. The outer body 100 is removable to facilitate instrument calibration and vehicle maintenance. When assembled on frame 116, outer body 100 forms a tight seal at the mounting interface to minimize fluid leakage into the suction zone.

Internal components include one or more vehicle and non-destructive test equipment control modules 118 and 119, internal inspection camera 96 with pan unit 97 and integrated lighting 98, and non-destructive test instruments with associated fixtures 123. It is also possible for the ROV 18 to carry other sensors and transducers, both internal and external to the outer body 100. Vehicle navigation lights 75 may be mounted internal to the ROV 18 in the positions illustrated in FIG. 8. The navigation lights will illuminate the area in front of the vehicle by projecting light through cutouts in the outer body 100. As noted above, ROV 18 carries a navigation camera 80, with integral tilt unit 73, and two laser sources 71 for calibration of dimensional gauging system. The two laser sources project parallel rays of laser light, with fixed, known spacing, onto the surface to be inspected. Surface features can be dimensionally gauged by imaging the feature of interest with the navigation camera 80, then scaling the image from the visible laser "dots" projected on the image by the two laser sources.

Suction plenums include one or more suction thrusters 122 which flow water from the suction plenums 120 in the directions indicated by arrows 124, and compliant skirt 127 mounted around the perimeter of the suction plenum 120. The compliant skirt 127 provides the interface between the suction plenum 120 and the hull, and functions to provide good conformance to rough, uneven or undulating hull surfaces, while generating minimal drag and compression forces. The result of the suction thrusters 122 in conjunction with the suction plenums 120 and compliant skirt 127 when the ROV is positioned or moving over the hull 11 of a ship, is to create a flow of water "under" ROV 18 in the directions indicated by arrows 126, as is illustrated most clearly in FIG. 8. The flow of water through the orifice formed by the intersection of the compliant skirt 127 and the hull surface results in a pressure drop in the direction of flow. Thus, suction plenum 120 will operate at reduced pressure relative to the external ambient pressure 121, causing ROV 18 to be forced by the pressure differential against the hull 11 of ship 10.

Free-flying and on-hull motive power is provided by drive propulsion modules 102. ROV 18 also comprises a third wheel 114, which is mounted for free rotation on a wheel support which rotates either freely in response to vehicle motion (passive wheel) or in controlled fashion in response to a control signal from the console to provide a steering function by movement of the wheel support subassembly in the directions of arrow 142 (actively controlled wheel). Wheel 114 is not driven, but merely serves to stabilize movement of the vehicle 18 on the surface of the hull 11 of the ship.

The construction of the drive propulsion module 102 is illustrated in detail in FIGS. 9 through 12. The construction of the drive propulsion module includes include thrusters 104 and drive wheels 106. Each of the thrusters 104 comprises a drive unit 130 coupled to a turbine 108. Each turbine 108 includes a propeller 110 and a nozzle 112. Power to the system is provided by a drive unit 130. Drive unit 130 can be any prime mover, including electric motor, hydraulic motor, or other. Thruster propeller 110 can be directly mounted to the rotational output shaft of drive unit 130, or mounted as a rotational element on a fixed support shaft 111 and magnetically coupled to the prime mover 130. Thruster nozzle 112 is mechanically supported from multiple struts eminating from the drive unit housing.

A drive pulley 132 and belt 133 couples power from the thruster 104 to a reduction gearbox 134. Belt 133 passes through a hole or slot 135 in thruster nozzle 112. Reduction gearbox 134, in turn, couples power to a drive shaft 136 which drives gears 138 and 140. Gear 140 is directly coupled to wheel 106.

In accordance with the present invention, ROV 18 is adapted and controllable to move in various directions corresponding to clockwise and counterclockwise movement of traction wheels 106. Likewise, steering may be provided by active rotation of follower wheel 102 in the directions indicated by arrow 142.

Figure 13:
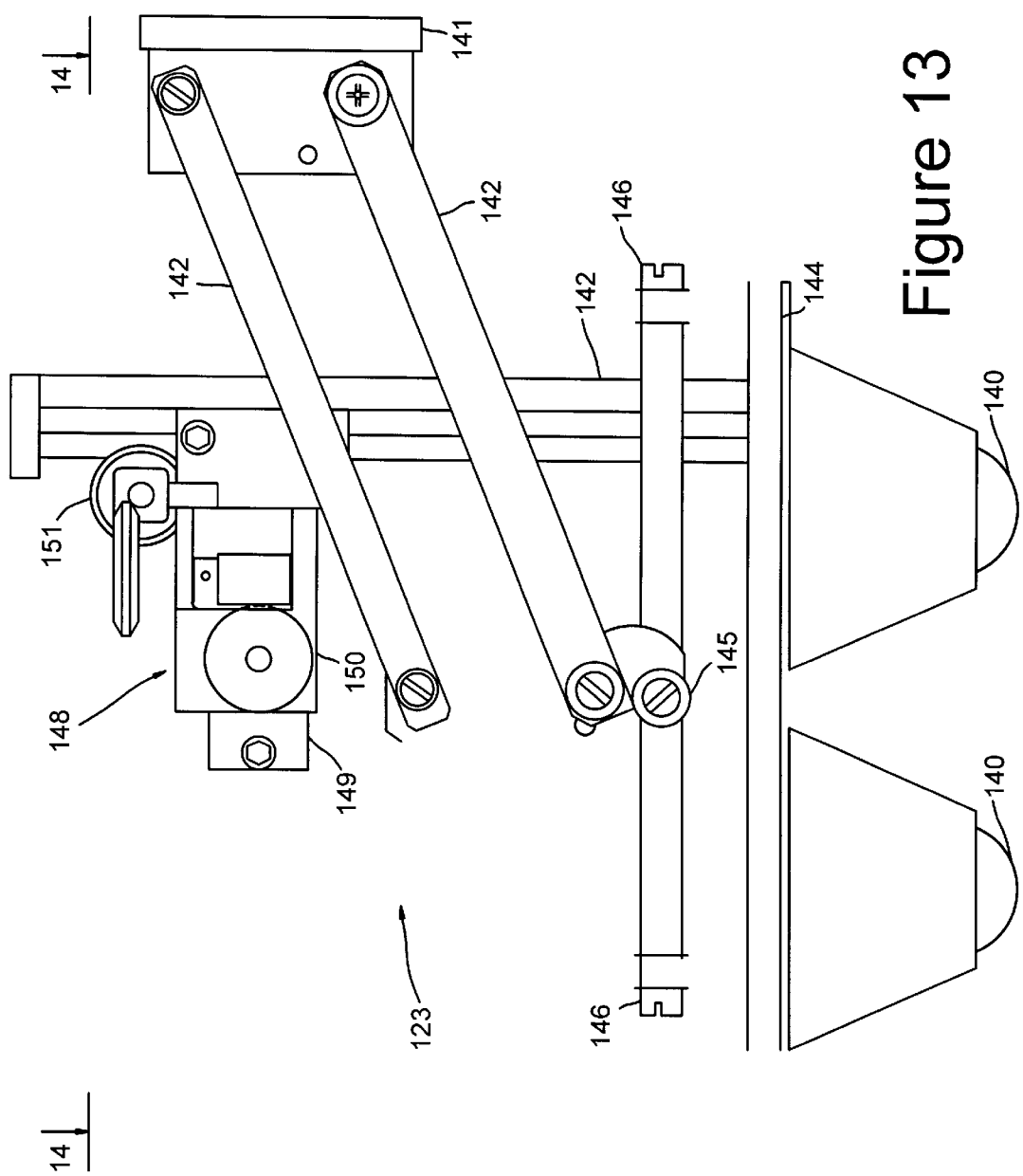
FIG. 13 is a elevational view of the NDT sled of present invention.
Figure 14:
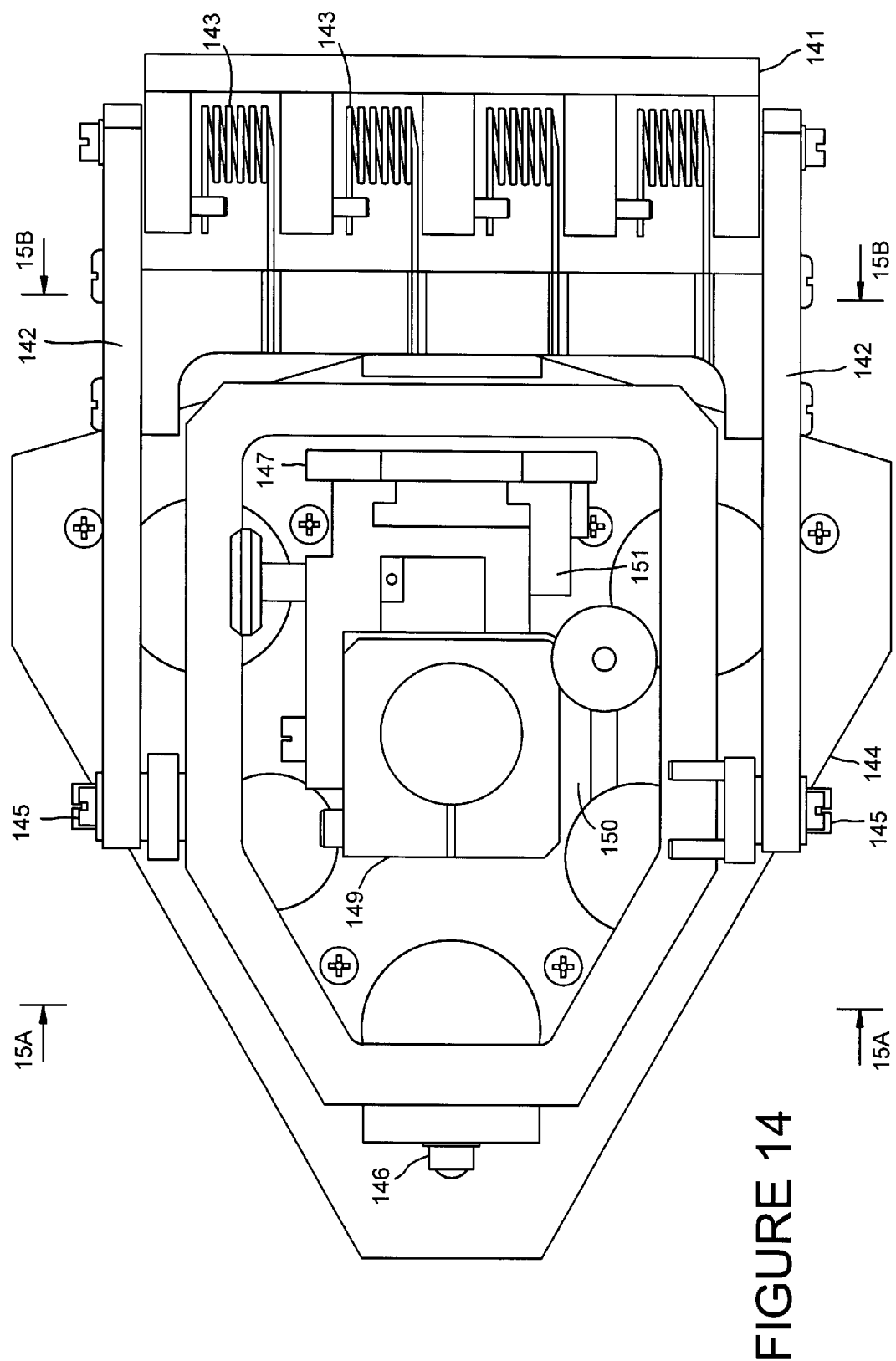
FIG. 14 is a plan view of the inventive NDT sled along lines 14—14 of FIG. 13.

The NDT transducer fixtures (NDT "sled" assemblies) 123 are illustrated in FIGS. 13 to 15. The NDT sled assemblies 123 maintain fixed transducer spacing (height above hull) and orientation relative to the local hull surface. The NDT sled assemblies are rigidly attached to the vehicle frame 116 via mounting plate 141, and are spring loaded against the hull surface via four-bar linkages 142 and springs 143. The NDT sled assembly base 144 is attached to four-bar linkage 142 via pivot pins 145 and 146. Pivot pins 145 permit limited (+/−30 degreees) pitch rotation (relative to horizontal) of the base assembly. Likewise, pivot pins 146 permit limited (+/−30 degreees) roll rotation (relative to horizontal) of the base assembly. The base includes 3 rolling or sliding contacts 140 which contact and move relative to the hull surface with low sliding or rolling friction. The 3 point hull contact provided by 140, in conjunction with the base pitch and roll degrees of freedom and spring loaded four-bar linkage permits the base 144 to assume an orientation parallel to the local hull surface as it travels over the hull.

Gimbal slide 147 is mounted to the base unit 144 in perpendicular fashion, as illustrated in FIG. 13. Gimbal slide 147 cross-section is T-shaped to accept mating transducer gimbal assembly 148 The transducer gimbal assembly 148 is free to slide vertically on the gimbal slide 147 and locked in position via set-screws at a desired height above the base unit 144. The transducer gimbal assembly 148 includes transducer clamp 149 for retaining cylindrical cross-sectioned transducers. The transducer clamp 149 couples to the gimbal slide 148 via pitch gimbal 150, and roll gimbal 151. The roll gimbal 151 contains a T-slot for mating to gimbal T shaped slide 147. Each gimbal axis includes knurled adjustment knobs connected to worm gearing for manual adjustment of the transducer orientation. The combined pitch and roll gimbals connecting the transducer clamp 149 to the gimbal slide 147 permits orientation of the transducer relative to the hull surface at a desired angle of operation. The gimbal slide and gimbal assembly 148 with transducer permits the distance between the clamped transducer face and the local hull surface to be adjusted by moving the gimbal assembly vertically on the slide, then locking it at the desired height. The NDT sled base 144 incorporates a through hole directly under the gimbal assembly to permit a direct water path between the clamped transducer and local hull surface.

Standard ultrasonic test transducers for metal thickness gauging are readily adapted to underwater service. The cylindrical shape of the ultrasonic transducers permits direct mounting in the NDT sled gimbal assembly clamp 149. The water path for the ultrasonic transducer is adjusted via the gimbal slide using the procedure describe above.

Standard eddy current transducers for coating thickness gauging and metal fracture detection are typically not rated for continuous underwater service. Additionally, for accurate coating thickness measurement, the flat face of the cylindrical eddy current transducer must maintain contact with the hull surface. The eddy current probe is adapted for this invention by housing it in a cylindrical water-tight tube, with replaceable end cap which maintains contact with the hull surface during the inspection process. The replaceable end cap is mad of suitable plastic material which provides low sliding friction, yet exhibits good resistance to abrasion. Once assembled in the water tight tube and placed in contact with the hull surface, the spacing between the eddy current transducer face and the hull is controlled by the thickness of the plastic endcap material between the hull contact face and the mating, internal transducer contact face. The water tight tube assembly with eddy current probe is spring loaded against the hull surface with enough force to maintain transducer contact with the hull. The NDT sled gimbal 148 assembly is adapted for the spring loaded eddy current transducer. A fixed clamp with mating T-slot is attached to the top of the gimbal slide 147. The gimbal assembly 148 with clamped eddy current probe in watertight container is mounted on the gimbal slide 147 in normal fashion, but the gimbal assembly 148 is not clamped in place, leaving it free to move in a vertical fashion on the slide. A compression spring is located between the fixed clamp and gimbal assembly 148, applying constant force to the eddy current water tight tube assembly in the direction of the hull surface. The compression spring is constrained by an internal metallic pin. The metallic pin is attached to the gimbal assembly 148 immediately adjacent to the gimbal slide 147, and running vertically parallel to the gimbal slide 147. The metallic pin is guided by and extends through a matched hole in the fixed clamp at the top of the gimbal slide 147. The compression spring is mechanically constrained throughout it's length by the internal pin and at it's ends by the gimbal assembly 148 and fixed clamp mounted to the top of the gimbal slide 147.

Figure 2:
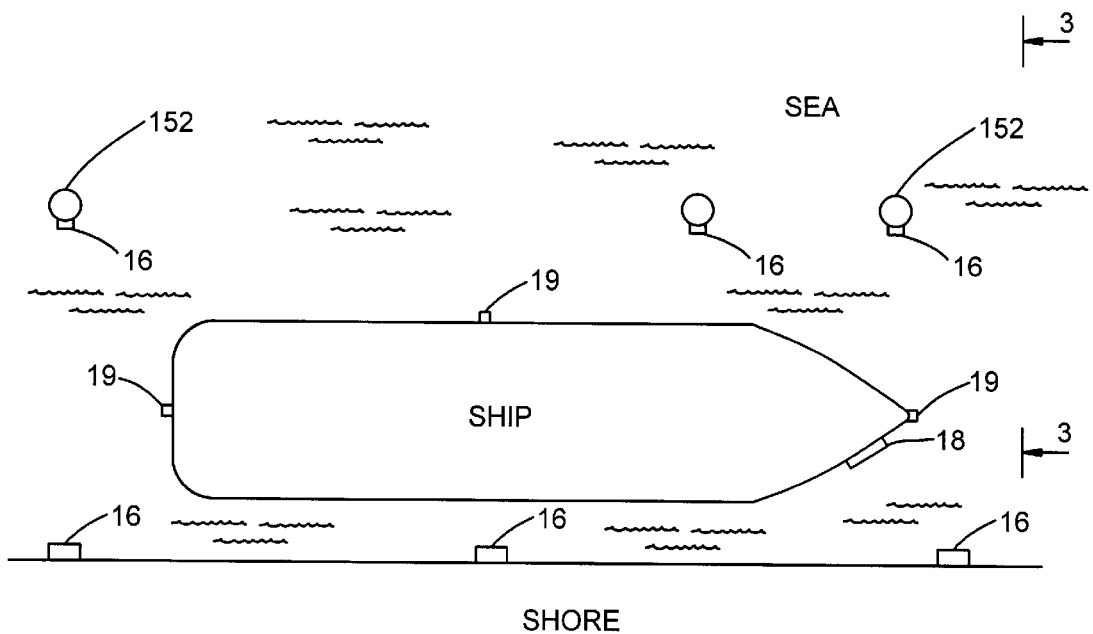
FIG. 2 is a plan view of a ship being inspected in accordance with the invention.

When it is desired to employ the system of the present invention, a ship 10 is brought into a facility where it may be docked in a stable manner. The inspection process can be carried out with the ship docked along a pier, moored within a harbor, or moored at open sea. After the ship 10 is securely docked or moored, a number of transceivers 16 are deployed at positions fixed with respect to the shore and the sea floor. Any convenient method of secure connection may be employed to achieve this result. In particular, transceivers 16 may be secured directly at positions on the bottom or the sides of the harbor or near the shore. A tripod 40 may also be used to position a transceiver 16 where the same may be otherwise difficult. Likewise, transceivers may be attached to piles 152 as illustrated in FIG. 2. The positions of transceivers 16 are selected to provide for line-of-sight acoustic communication between the transceivers 16 and similar transceivers on ROV 18. Once this has been achieved, the position of the ship may be determined by the placement of transceivers 19 on the ship, for example, at the positions illustrated in FIG. 2 along the centerline of the ship and about 2 meters below the surface.

After the fixed transceivers 16 have been placed in the desired positions, and the position of the ship made possible to determine through the placement of transceivers 19 on the hull 11 of the ship, ROV 18 is introduced into the water and caused to swim, unmanned, to the hull 11 of the ship through the use of its thrusters 104, which propel it through the water to the hull 11 of the ship. Complete control of the flight path of the ROV 18 during the transit to the hull is achieved by varying the propulsion thrust in a forward/aft direction and vertical direction, and by varying the thrust generated moments for yaw, pitch and roll. Forward/aft directional control is provided by the drive propulsion modules 102 acting in unison. Vertical directional control is provided by the suction thrusters 122 and 128. Vehicle yaw control is provided by asymmetrical operation of drive propulsion modules 102. Likewise, vehicle pitch and roll control is provided by asymmetrical operation of suction thrusters 122.

During the flight from the point of deployment to the hull 11 of the ship, ROV 18 is caused to swim underwater. Navigation may be automatically controlled by the computer network 20 during the initial part of the swim, or the same may be completely manually controlled. During the portion of the swim during which ROV 18 "lands" on the hull 11 of ship 10, the same may be performed under manual control of an operator at the console. The operator is presented with visual data during this part of the operation through the use of the navigation camera. In principle, the same may be assisted through the use of sonar or other appropriate instrumentation.

If the shape of a ship being surveyed is known, for example, based upon the plans used when it was being built, or based upon another survey conducted in accordance with the present invention, the ROV 18 may be caused to move automatically along a predetermined path. If, on the other hand, no such information exists, various instrumentation on the ROV may be used to cause it to move along a path defined by the intersection of the hull 11 of the ship 10 and the surface of the sea. After this shape has been defined, the ROV 18 can be caused to travel along paths at successfully lower levels until the entire surface of the ship is covered. Likewise, the inspection path can be controlled to follow lines of constant girth, with the vehicle traveling between port side water line and starbord side waterline, advancing bow to stern or stern to bow at the completion of each waterline to waterline pass.

The inspection of the hull 11 is carried on both electronically and visually during the course of such movement. It is contemplated in accordance with the present invention, because of the shape of many hulls 11, operator intervention and/or guidance would be a part of the control of the movement of ROV 18. Such operator intervention is guided by readings on instruments which show the depth, position and orientation of the ROV as well as the display of the environment surrounding the ROV 18, which display is provided by the navigation camera 80 and inspection camera 121. After the survey and primary inspection of the hull 11 has been carried on with reference to the information produced by the various inspection devices on board the ROV 18 and with reference to the visual inspection of the hull 11 provided by the navigation and inspection cameras, problem areas on the hull are likely to be identified and targeted for a slower, and perhaps slightly or dramatically different, inspection protocol.

Figure 16:
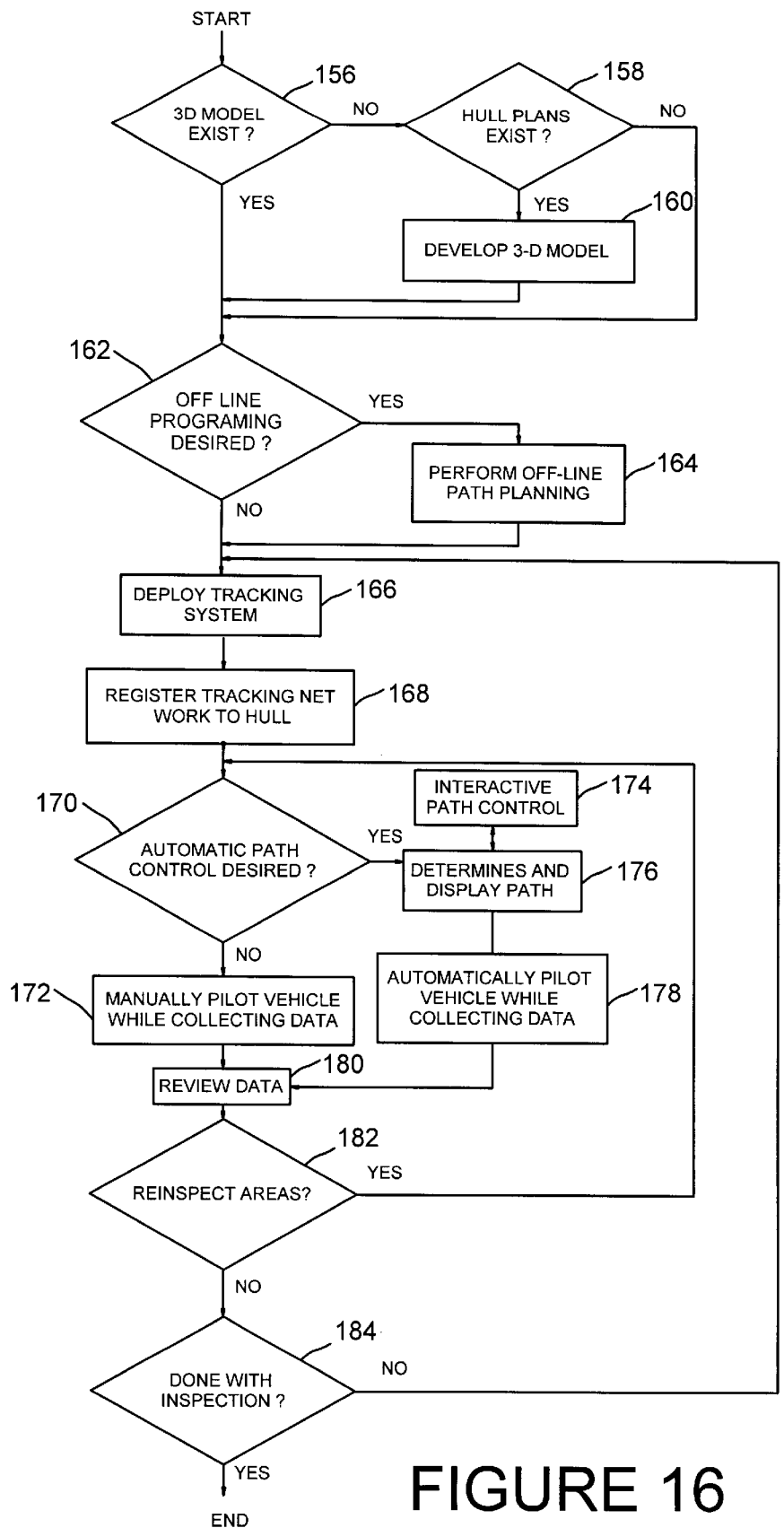
FIG. 16 is a flow chart illustrating the inventive process for inspection of a submerged structure.

The overall inspection process is outlined in FIG. 16. Referring to FIG. 16, the process begins by determining at step 156 whether there is an existing 3-D model of the shape of the hull 11 of the ship. If such a model exists, the software proceeds from step 156 to step 162 where it is determined if the inspection path is to be pre-programmed "off-line" (prior to the inspection). If it is desired to plan the inspection path off-line, then step 164 is performed to generate the inspection path plan. In step 164, there are several options for generating the inspection path plan. If the ship has been previously inspected using the process described by this invention, the planned inspection path can be based on a previously stored inspection path. If there is no stored inspection path plan for the ship, then the inspection path planning can be performed using a dedicated software program which accepts the 3-D hull shape model filename as input, and generates as output a file containing a series of straight line motion segments to be executed by the ROV control system during actual survey. Each straight line motion segment consists of a segment endpoint (desired final location and orientation of the ROV at the terminus of the straight line move), desired path velocity, and desired path acceleration. Generation of the straight line motion segments comprising the inspection path can be performed automatically or manually. If generated automatically, the path planning program will automatically create a series of inspection paths according to one or more of the methods which were described above. One method generates a series of inspection paths parallel to the ship's waterline. A second method generates a series of parallel paths around the girth of the ship, up to the ship's waterline. If generated manually, the inspection path will be created by an operator manually defining (via mouse or other input device) the straight line segments on the 3-D hull image displayed on the computer console.

If, at step 156, it is determined there is not an existing 3-D model of the shape of the hull 11 of the ship, then the availability of ship hull plans from which a 3-D hull shape image can be created is determined (step 158). Appropriate plans for 3-D hull shape model generation include ship plate expansion drawings in conjunction with CAD generated 3-D hull form description drawings or ship table of offsets used for hull manufacture. Additionally, ship data such as forward, aft and mid-section drafts may be useful for inspection path planning performed at step 164. If it is determined at step 158 that appropriate plans and data exist for 3-D hull model generation, then a dedicated software program can be used to generate the 3-D hull shape model in step 160. The dedicated software program will accept the filenames for the various ship plans and data as input, and generate the 3-D hull shape model file as output. Some forms of ship plans to be input, such as plate expansion drawings, may exist in paper drawing form only. In cases such as this, the plan may require digitization by manual methods (i.e., digitizing tablet) or automatic methods (i.e., scanner plus CAD program) prior to input for the 3-D hull shape model generation process.

If at step 158 it is determined that appropriate ship plans required for 3-D ship hull shape model do not exist, then, during the course of a normal hull inspection (starting at step 166), the ROV and associated tracking system can be used to generate the ship's 3-D hull shape in a form suitable for 3-D hull shape model generation. Hull profile data can be generated by driving the ROV over the submerged hull surface while tracking and recording (on non-volitile media) the vehicle's position and orientation using the acoustic tracking system and ROV instrumentation. The recorded hull profile data can then be used as input to a dedicated software program for generation of 3-D hull shape model from vehicle position and orientation tracking data. Additionally, the ROV and associated tracking system can be used to identify and record the positions of the ship's plate vertices for incorporation of plate geometry information into the 3-D hull shape model.

The on-hull survey starts at step 166. The first step in the process (step 166) is deployment of the acoustic tracking system per methods described previously. After deployment of the acoustic network, the network is registered to the ship's hull in step 168. This process involves driving the ROV to 3 positions on the submerged portion of the hull within the range of the acoustic network, and recording the positions (in acoustic network based coordinates) of three hull features with known locations in the hull based reference frame. The control software program operating in the navigation computer 42 is then directed to translate the acoustic network reference frame to the hull based reference frame. Following completion of step 168, all ROV position and orientation data generated by the acoustic tracking system will be referenced to the hull based reference frame.

After deployment and registration of the acoustic tracking system in steps 166 and 168, the ROV is directed to proceed to the inspection steps. At step 170, if it is determined that automatic ROV path control is not desired, then the operator can manually pilot the vehicle to conduct the on-hull inspection in step 172. During manual operation, the ROV is manually piloted over the surface of the hull, while the NDT instrumentation continuously tests and records the condition of the hull 11. If automatic ROV path control is selected at step 170, then the pre-planned path is displayed by the monitor in step 174, and means are provided in the form of step 176 for a human operator to edit the path calculated by the computer. At completion of pre-planned path display and review, the operator then directs the computer to proceed to step 178 and controls the ROV to follow the prescribed inspection path. While this is being done the computer also directs the ROV NDT instrumentation to test and record the condition of the hull 11. During this part of the operation, the computer is responsive to manual input control by a human operator who views the environs of the ROV through the navigation camera.

At completion of the planned inspection path sequence in which data has been gathered and recorded with respect to position and the corresponding hull 11 condition, the operator is given the opportunity to review the hull condition data (step 180), and, if available, historical data for the same ship. After review of the survey data in step 180, the operator determines in step 182 whether more information needs to be taken in certain areas through the use of a detailed survey of that area, as discussed above. If specific areas are in need of more detailed inspection, the sequence repeats from step 170. If there is no need to further inspect the hull within the current area of coverage provided by the acoustic tracking network, then it is determined at step 184 whether the complete submerged surface of the hull has been inspected. If there are additional areas of the submerged hull that require inspection, and additionally, require repositioning of the acoustic tracking network to provide required tracking coverage, then the sequence starting at step 166 is repeated. If there are no additional areas of the submerged hull to be inspected, then the survey portion of the process is complete, and data post-processing can be started.

Figure 17:
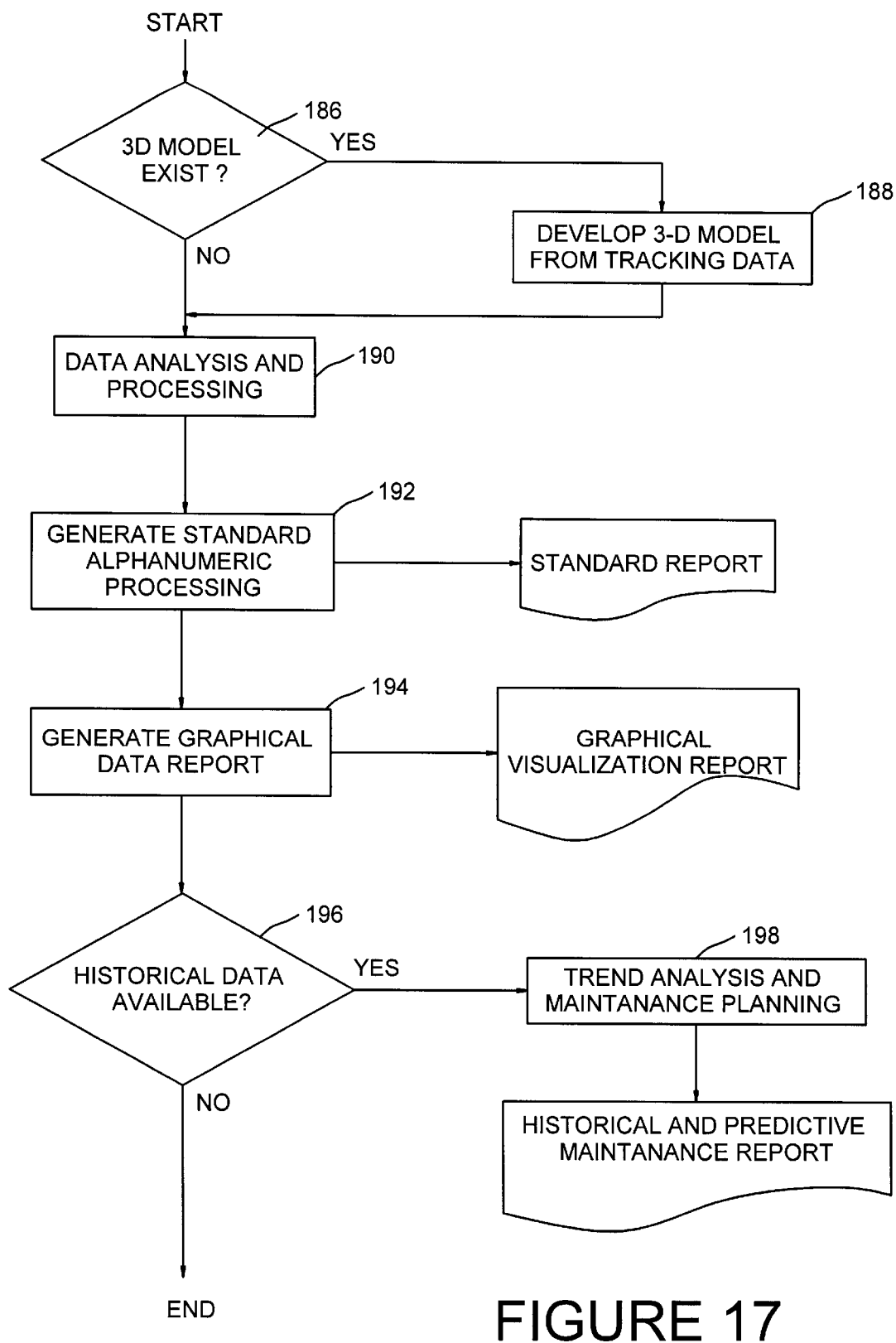
FIG. 17 is a flow chart illustrating the inventive process for post processing and data reporting of data gathered by the inventive process of FIG. 16.

The overall post-processing operation is outlined in FIG. 17. Referring to FIG. 17, the process begins by determining at step 186 whether a it is desired to develop a 3-D model of the shape of hull from the acquired and recorded survey tracking data. If existing hull shape models do not exist, or the hull plans required to construct a 3-D hull shape model do not exist, then an empirical model can be developed in step 188 from the ROV tracking data taken during a survey. Additionally, if 3-D hull shape models do exist, it may still be desirable to generate an empirical model from actual survey tracking data for model refinement purposes.

In step 190, the acquired data is analyzed and processed for data reporting and visualization. This step may involve identification and removal of "bad" data from the data set, data filtering (smoothing), data tagging (a hull plate identification can be associated with each data sample, based on sample location on the hull), and data statistical analysis. An industry standard alphanumeric text report is generated in step 192, consisting of tabulated NDT data measurements (hull thickness, coating thickness, cathodic protection device potential, etc.) and the positions on the hull where the measurements were taken. Additionally, the data can be sorted and reported on a hull plate by plate basis. Graphical representations of the survey data are generated in step 194. Graphical representations include two dimensional and three dimensional views of the hull or sections of the hull, with the data value at a location on the surface encoded using color, texture, or height above the surface. Hull material cross-sections can be generated along operator defined lines of intersection (e.g., making it possible to view hull thickness at a specified cross-section of the ship).

In addition to printed reports, all reports generated by the process described by this invention can be delivered in various "electronic" formats to the end user. The tabulated and graphical data reports can be converted to HTML files, making it possible for the customer to review the survey reports using a standard internet web browser. The HTML report files can be delivered on CD media for "local" browsing on a customer's PC, or the files can be embedded within a password protected web site for review over the internet.

In step 196, it is determined if historical survey data exists for the specific ship. If previous survey data generated by the process covered by this invention exists, then step 198 can be used to provide documented hull condition trend analysis and predictive maintenance planning. It is also contemplated that changes in the overall shape of the inspected structure as compared to construction plans and/or a prior survey or surveys may indicate particular problems and appropriate measures taken.

Figure 18:
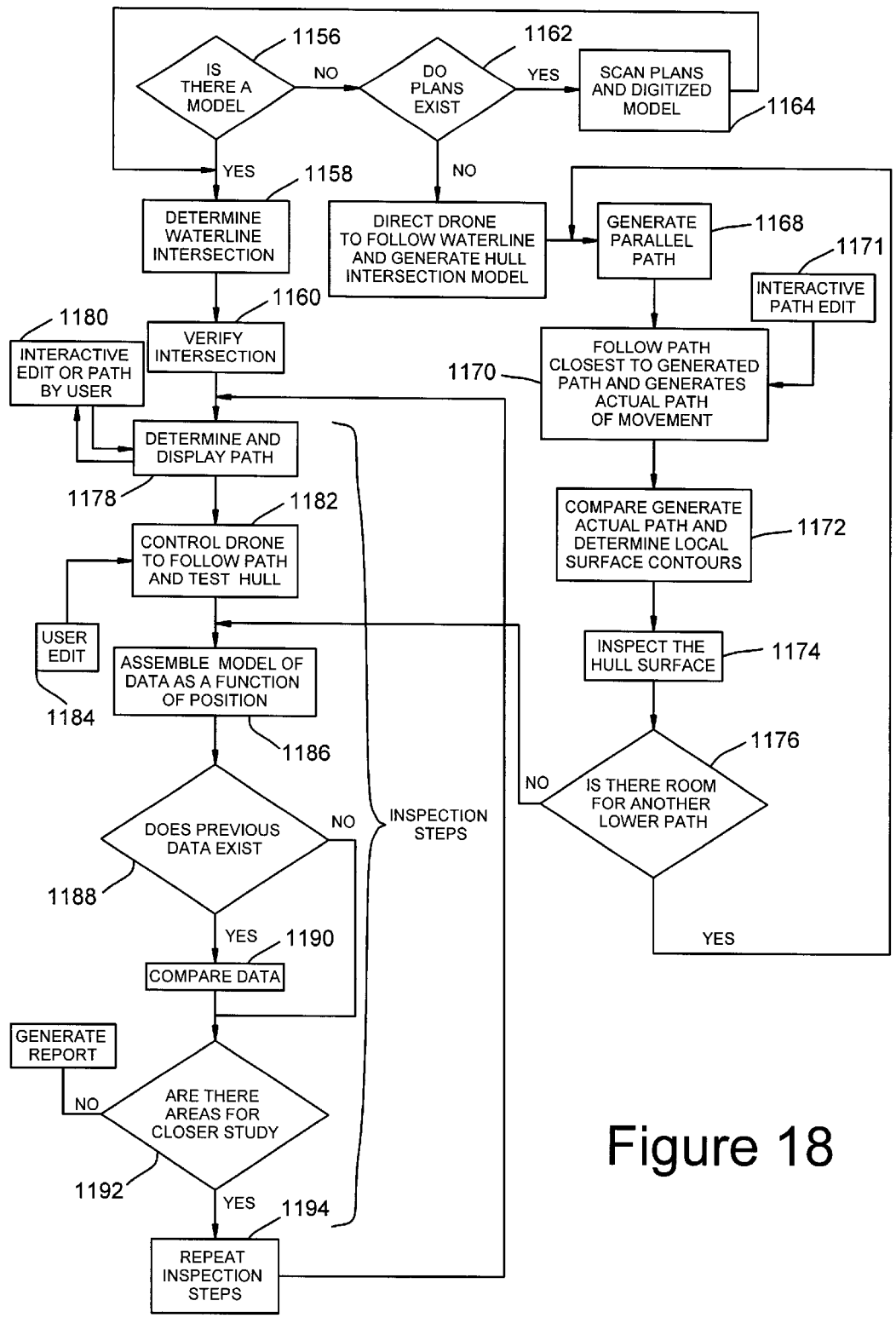
FIG. 18 is a flow chart illustrating an alternative embodiment of the inventive software that controls the inventive apparatus.
Figure 19:
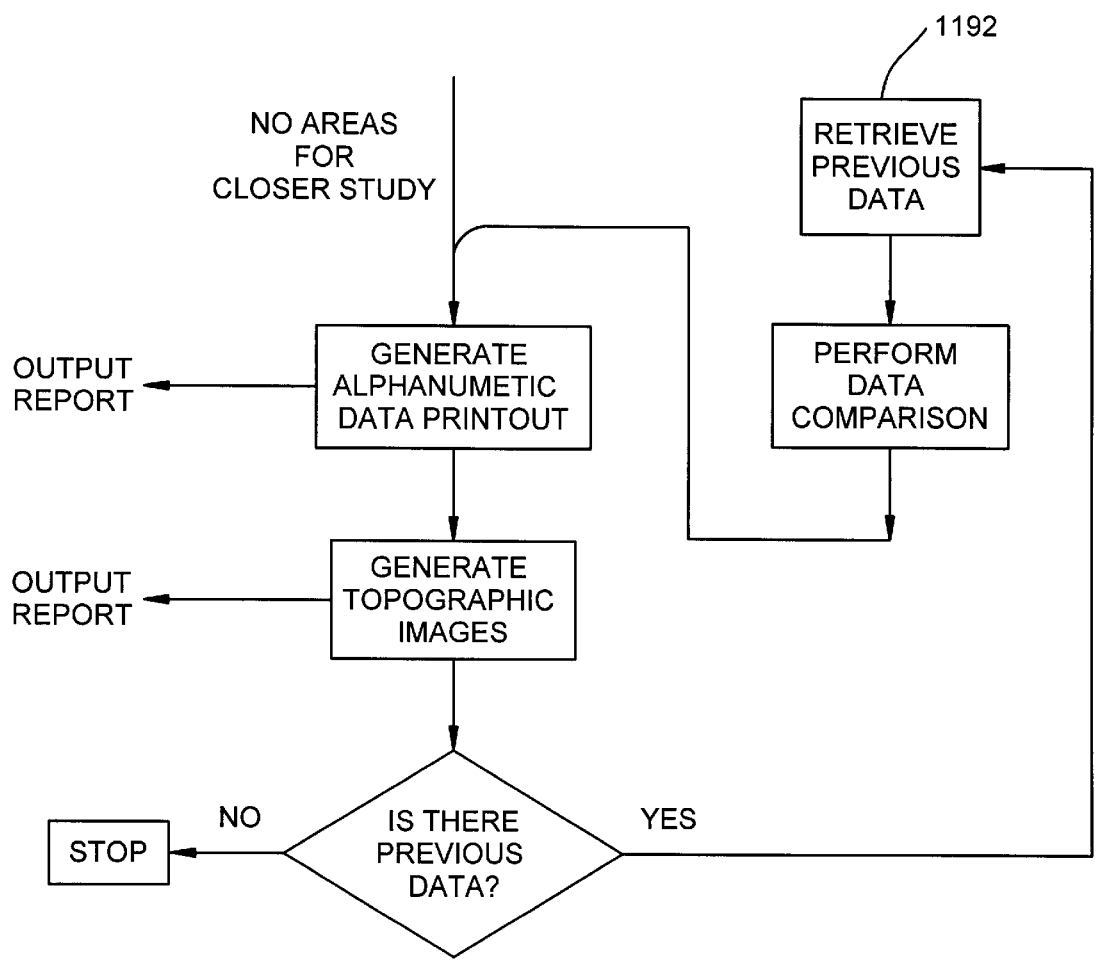
FIG. 19 is a detailed drawing of a portion of the software of FIG. 18.

Alternatively, computers 42, 44 and 76 cooperate to execute the software algorithm of the present invention. Referring to FIG. 18, generally similar components or parts performing analogous, corresponding or identical functions to those of the previous embodiment are numbered herein with numerals which differ from the previous embodiment by multiples of one thousand. The alternative process, begins by determining at step 1156 whether there is an existing model of the shape of the hull 11 of the ship. If such a model exists, the software proceeds from step 1156 to subroutine 1158 where a determination of the intersection of the surface of the sea and the hull 11 of the ship when the ship is afloat is made.

Once the shape and position of the intersection in space has been determined by subroutine 1158, the ROV 18 is caused to travel along the shape surface of the hull 11 corresponding to the intersection in order to verify the accuracy of the computer generated intersection shape and position. Subroutine 1160 thus comprises a sequence of thruster commands and position sensing commands responsive to positional information feedback to cause the ROV to trace the shape of the intersection on the hull 11 of the ship at a point just below the surface of the water. Thereafter, the hull is surveyed by the ROV in the manner detailed below.

If there is no model of the shape of the hull 11 of the ship, at step 1162, the question is asked whether plans for the ship exist. If such question, which is shown on the screen of the computer, is answered in the affirmative, the user is directed to put the plans on a scanner and the program proceeds to subroutine 1164, which is a package for scanning such plans and artificially generating a three dimensional picture in space as a matrix of numbers which describe the shape of the hull 11 of the ship. Once this has been done, subroutine 1164 directs the machine to proceed to subroutine 1158. In this regard, the information respecting the weight of the ship is also introduced into subroutine 1158 in order to determine the waterline based on displacement of a volume of water equal to the weight of the ship.

After such determination has been made at subroutine 1158, the shape of the intersection and its position is verified by subroutine 1160, by an attempt by the ROV to trace the shape in the water.

After the shape of the intersection has been verified, the computer proceeds to the inspection steps.

If no plans exist for the ship, it is necessary to generate some hull 11 shape information. This is done by the computer using subroutine 1166 to direct the ROV to trace the shape of the intersection by crawling around the hull 11 while trying to stay just below the waterline. In doing this work, a depth transducer adapted to provide very accurate depth information at depths close to the surface may be used as a feedback device when such transducer is mounted on ROV 18. This information can be input into the computer to allow the computer to generate appropriate control signals to cause the ROV to trace the intersection, while the position determining ultrasonic system gathers intersection shape information.

The movement of ROV 18 is controlled by subroutine 1166. After the intersection has been determined, ROV 18 is directed to proceed along a path parallel to the intersection and displaced downwardly from the intersection by a desired distance. This is achieved by subroutine 1168, which provides this function in a manner substantially similar to similar functions in computer aided drafting applications and based upon an operator input or computer generated prediction of below the water hull shape.

After the parallel path has been generated, subroutine 1170 controls ROV 18 to follow a path on the hull 11 as close as possible to the generated parallel path and to generate actual path shape based on its movement. During the execution of subroutine 1170, the navigation camera on board ROV 18 provides a display to the operator at the console, and the human operator may vary the path followed by the ROV through an interactive subroutine 1171.

At the same time, subroutine 1172 is comparing actual path of movement information to generated path information to determine the difference between predicted hull shape and the actual contours of the area of the hull that the ROV is passing over. At the same time, a separate subroutine 1174 provides the computer network 20 in the console with measurement information from the various transducers on the ROV in order to map inspection information on the condition of the hull 11.

Next, at step 1176, the question is asked by the computer as to whether it appears that the entire surface of the ship that is underwater have been surveyed. If the answer is yes, a complete map of the shape of the hull 11 has been produced and this information can then be used to proceed to the detailed portion of the inspection, as will be described below. If more of the hull 11 needs to be surveyed, the computer is directed to return to subroutine 1168 and generate the next lower parallel path. This process is repeated until the entire hull 11 is surveyed.

In the case of an inspection of a hull 11 for which there is a model, after the shape of the intersection has been verified at step 1160, the machine is directed to proceed to the inspection steps. The first of these inspection steps is subroutine 1178 which determines and displays the path for the ROV 18 to follow in order to inspect the entire surface of the hull 11 of the ship. The path is displayed by the monitor and means are provided in the form of a subroutine 1180 for a human operator to edit the path calculated by the computer operating in accordance with subroutine 1178. The computer then proceeds to step 1182 and controls the ROV to follow the path determined by subroutine 1178 as edited by subroutine 1180. While this is being done the computer also directs the ROV instrumentation to test the condition of the hull 11. During this part of the operation, subroutine 1182 is responsive to human user input control provided by subroutine 1184. Such interactive human intervention is provided by a human operator who views the environs of the ROV through the navigation camera.

After data has been gathered with respect to position and the corresponding hull 11 condition, whether through the completion of subroutine 1182 or the answering in the negative of the question of step 1176, the computer is directed to proceed to assemble a model of the data as a function of position through the execution of subroutine 1186.

After this is done, at step 1188, the question is asked as to whether previous data exists. If the answer is in the affirmative, the data is secured and a comparison is made by the computer at step 1190. If no such data exists, the computer proceeds directly to step 1192 where a subroutine determines whether or not closer inspection of some areas is necessary.

Likewise, it there is available data and subroutine 1190 has made a comparison, that information is output, together with the recent data to subroutine 1192 to make a determination as toward whether more information needs to be taken in certain areas through the use of a detailed survey of that area, as discussed above. If the determination is made that such additional detailed inspection needs to be done, step 1194 directs the system to repeat subroutines and steps 1186 through 1192. Once step 1192 is performed and a determination is made that no further detailed inspection is necessary, the report subroutine 1196 is actuated, report printed and the inspection is complete.

In accordance with the present invention, it is also contemplated that changes in the overall shape of the inspected structure as compared to construction plans and/or a prior survey or surveys may indicate particular problems and appropriate measures taken. Likewise, historical tracking of deterioration in long and short term conditions to optimize the time at which the problem is addressed is possible and contemplated to be within the scope of the invention.

While an illustrative embodiment of the invention has been described above, it is, of course, understood that various modifications will be apparent to those of ordinary skill in the art. Such modifications are within the spirit and scope of the invention, which is limited and defined only by the appended claims.

What is claimed is:

1. An in-water ship hull inspection system for inspection of the submerged portion of the hull of a ship floating in a body of water, said inspection system comprising:
   (a) a remotely operated vehicle, said remotely operated vehicle comprising:
   (i) a remotely operated vehicle body having a first surface portion, said first surface portion being configured to be oriented towards and supported in a hull inspection position against the hull of a ship to be inspected;
   (ii) a water moving device for moving water located between said first surface portion and said hull of said ship through said remotely operated vehicle body thereby creating a pressure drop between said first surface portion and said hull, said pressure drop being sufficient to result in a force urging said remotely operated vehicle toward said hull;
   (iii) a propulsion mechanism coupled to said body, said propulsion mechanism having at least one thruster, said thruster having the ability to propel said remotely operated vehicle through said body of water toward and onto said hull in said hull inspection position;
   (iv) a drive mechanism coupled to said remotely operated vehicle body, said drive mechanism having drive wheels which can be rotated, when said remotely operated vehicle is in said hull inspection position, rotation of said drive wheels propelling said remotely operated vehicle along said ship hull; and (v) an acoustic transducer located on said remotely operated vehicle body;

(b) a testing device, said testing device being coupled to said remotely operated vehicle body, and said testing device comprising instrumentation capable of examining the integrity and structure of said ship hull;

(c) a first plurality of acoustical devices located on the hull of the ship to be inspected, said acoustical devices having fixed positions with respect to said hull;

(d) a second plurality of acoustical devices located in the vicinity of the hull of the ship to be inspected, said second plurality of acoustical devices adapted to be positioned in fixed positions with respect to the floor of said body of water, and said acoustic transducer and said first and said second plurality of acoustical devices together forming an acoustical network outputting data;

(e) a computer system, said computer system being coupled to said acoustical network, said computer system transforming data from said acoustical network into positional data.

2. A system as in claim 1, wherein said remotely operated vehicle is substantially sealed to said hull.

3. A system as in claim 1, wherein said drive wheels can be rotated in either direction.

4. A system as in claim 1, wherein said second plurality of acoustic devices is acoustically coupled to said first plurality of acoustical devices, and said second plurality of acoustical devices being acoustically coupled to said acoustic transducer located on said remotely operated vehicle body.

5. A system as in claim 1, wherein said positional data includes remotely operated vehicle positional data, said remotely operated vehicle positional data being determined by said computer system based on the time it takes for an acoustic pulse to travel between said acoustic transducer located on said remotely operated vehicle body and said second plurality of acoustical devices, said positional data including hull orientation data calculated by said computer system based on the time takes for an acoustic pulse to travel between said second plurality of acoustical devices and said first plurality of acoustical devices, said position control computer being able to calculate the on hull position of said remotely operated vehicle based on said remotely operated vehicle positional data relative to said hull orientation data.

6. A system as in claim 1, wherein said computer system is coupled to said propulsion mechanism and said drive mechanism on set remotely operated vehicle body to control the position of said remotely operated vehicle by controlling the propulsion and/or drive mechanisms of said remotely operated vehicle.

7. A remotely operated underwater vehicle, adapted to move along the surface of a submerged structure in a body of water, comprising:

(a) a remotely operated vehicle body having a first surface portion, said first surface portion being configured to be oriented towards and supported in an operating position against said surface of said submerged structure;

(b) a water moving device for moving water located between said first surface portion and said surface of said submerged structure through said remotely operated vehicle body thereby creating a pressure drop between said first surface portion and said surface of said submerged structure, said pressure drop being sufficient to result in a force urging said remotely operated vehicle toward said surface of said submerged structure (c) support structure consisting of only three wheels mounted on said remotely operated vehicle body to support said remotely operated vehicle body on the hull of a ship on portions of said hull which are underwater.

8. A remotely operated underwater vehicle as in claim 7, wherein a propulsion mechanism is coupled to said body, said propulsion mechanism having at least one thruster, said thruster having the ability to propel said remotely operated vehicle through a body of water toward and onto said submerged structure in said operating position.

9. A remotely operated underwater vehicle as in claim 7, wherein a drive mechanism is coupled to said remotely operated vehicle body, said drive mechanism having drive wheels which can be rotated when said remotely operated vehicle is in said operating position, rotation of said drive wheels propelling said remotely operated vehicle along said submerged structure.

10. A remotely operated underwater vehicle as in claim 8, wherein a drive mechanism is coupled to said remotely operated vehicle body, said drive mechanism having drive wheels which can be rotated when said remotely operated vehicle is in said operating position, rotation of said drive wheels propelling said remotely operated vehicle along said submerged structure.

11. A remotely operated underwater vehicle as in claim 7, wherein a testing device is coupled to said remotely operated vehicle body, said testing device comprising instrumentation capable of examining the integrity and structure of said submerged structure.

12. A remotely operated underwater vehicle as in claim 7, wherein a first plurality of acoustical devices is located in the vicinity of said submerged structure to be inspected, said first plurality of acoustical devices adapted to be positioned in fixed positions with respect to the floor of said body of water.

13. A remotely operated underwater vehicle as in claim 7, wherein a second plurality of acoustical devices is located on the surface of said submerged structure to be inspected, said second plurality of acoustical devices having fixed positions with respect to said submerged structure, and said acoustic transducer and said first and said second plurality of acoustical devices together forming an acoustical network outputting data.

14. A remotely operated underwater vehicle as in claim 13, wherein a computer system is coupled to said acoustical network, said computer system transforming data from said acoustical network into positional data.

15. A remotely operated underwater vehicle as in claim 14, wherein said positional data includes remotely operated underwater vehicle positional data, said remotely operated underwater vehicle positional data being determined by said computer system based on the time it takes for an acoustic pulse to travel between said acoustic transducer located on said remotely operated vehicle body and said first plurality of acoustical devices, said positional data including submerged structure orientation data calculated by said computer system based on the time takes for an acoustic pulse to travel between said first plurality of acoustical devices and said second plurality of acoustical devices, said position control computer being able to calculate the on-structure position of said remotely operated underwater vehicle based on said remotely operated underwater vehicle positional data relative to said submerged structure orientation data.

16. An in-water inspection system for inspection of the submerged portion of a structure in a body of water, said inspection system comprising:
  (a) a remotely operated inspection vehicle having an acoustic transducer said remotely operated vehicle comprising:
    (i) a remotely operated vehicle body having a first surface portion, said first surface portion being configured to be oriented towards and supported in an operating position against said surface of said submerged structure; and
    (ii) a water moving device for moving water located between said first surface portion and said surface of said submerged structure through said remotely operated vehicle body thereby creating a pressure drop between said first surface portion and said surface of said submerged structure, said pressure drop being sufficient to result in a force urging said remotely operated vehicle toward said surface of said submerged structure;
  (b) a first plurality of acoustical devices located in the vicinity of the structure to be inspected, said first plurality of acoustical devices adapted to be positioned in fixed positions with respect to the floor of said body of water, and said acoustic transducer and said first plurality of acoustical devices together forming an acoustical network outputting data; and
  (c) a computer system, said computer system being coupled to said acoustical network, said computer system transforming data from said acoustical network into positional data.

17. An inspection system as in claim 16, wherein a testing device is coupled to said remotely operated vehicle body, said testing device comprising instrumentation capable of examining the integrity and structure of said submerged structure.

18. A method of inspecting the submerged portion of the hull of a ship in a body of water, comprising the steps of:
  (a) deploying a first plurality of acoustical devices located on the hull of the ship to be inspected, said acoustical devices having fixed positions with respect to said hull;
  (b) deploying a second plurality of acoustical devices located in the vicinity of the hull of the ship to be inspected, said second plurality of acoustical devices being adapted to be positioned in fixed positions with respect to the floor of said body of water;
  (c) navigating a remotely operated vehicle toward and along the surface of said hull, said remotely operated vehicle having:
    (i) a testing device comprising instrumentation capable of generating examination data by examining the integrity and structure of said hull;
    (ii) a remotely operated vehicle body having a first surface portion, said first surface portion being configured to be oriented towards and supported in a hull inspection position against the hull of a ship to be inspected;
    (iii) a water moving device for moving water located between said first surface portion and said hull of said ship through said remotely operated vehicle body thereby creating a pressure drop between said first surface portion and said hull, said pressure drop being sufficient to result in a force urging said remotely operated vehicle toward said hull; and
    (iv) an acoustic transducer, said acoustic transducer and said first and said second pluralities of acoustical devices together forming an acoustical network outputting data;
  (d) transforming data from said acoustical network into positional data by use of a computer system coupled to said acoustical network; and
  (e) using said positional data to correlate said examination data with locations on said hull.

19. A method as in claim 18, wherein said remotely operated vehicle further comprises:
  (a) a propulsion mechanism coupled to said body, said propulsion mechanism having at least one thruster, said thruster having the ability to propel said remotely operated vehicle through said body of water toward and onto said hull in said hull inspection position; and
  (b) a drive mechanism coupled to said remotely operated vehicle body, said drive mechanism having drive wheels which can be rotated, when said remotely operated vehicle is in said hull inspection position, rotation of said drive wheels propelling said remotely operated vehicle along said ship hull.

20. A method as in claim 19, wherein a testing device is coupled to said remotely operated vehicle body, said testing device comprising instrumentation capable of examining the integrity and structure of said hull.

21. A method as in claim 19, wherein said positional data includes remotely operated vehicle positional data, said remotely operated vehicle positional data being determined by said computer system based on the time it takes for an acoustic pulse to travel between said acoustic transducer located on said remotely operated vehicle body and said second plurality of acoustical devices, said positional data including hull orientation data calculated by said computer system based on the time takes for an acoustic pulse to travel between said first plurality of acoustical devices and said second plurality of acoustical devices, said position control computer being able to calculate the on-hull position of said remotely operated vehicle based on said remotely operated vehicle positional data relative to said hull orientation data.

22. A remotely operated underwater vehicle as in claim 7 further comprising an acoustic transducer capable of transmitting high-frequency acoustic pulses said acoustic transducer having a fixed position with respect to said first surface portion.

23. An in-water ship hull inspection system for inspection of the submerged portion of the hull of a ship floating in a body of water, said inspection system comprising:
  (a) a remotely operated vehicle, said remotely operated vehicle comprising:
    (i) a remotely operated vehicle body having a first surface portion, said first surface portion being configured to be oriented towards and supported in a hull inspection position against the hull of a ship to be inspected;
    (ii) a water moving device for moving water located between said first surface portion and said hull of said ship through said remotely operated vehicle body thereby creating a pressure drop between said first surface portion and said hull, said pressure drop being sufficient to result in a force urging said remotely operated vehicle toward said hull;
    (iii) a propulsion mechanism coupled to said body, said propulsion mechanism having at least one thruster, said thruster having the ability to propel said remotely operated vehicle through said body of water toward and onto said hull in said hull inspection position; and
    (iv) a drive mechanism coupled to said remotely operated vehicle body, said drive mechanism having drive wheels which can be rotated, when said remotely operated vehicle is in said hull inspection position, rotation of said drive wheels propelling said remotely operated vehicle along said ship hull;

(b) a testing device, said testing device being coupled to said remotely operated vehicle body, and said testing device comprising instrumentation capable of examining the integrity and structure of said ship hull.

24. An in-water ship hull inspection system as in claim 23, further comprising:

(c) a first plurality of acoustical devices located on the hull of the ship to be inspected, said acoustical devices having fixed positions with respect to said hull;

(d) a second plurality of acoustical devices located in the vicinity of the hull of the ship to be inspected, said second plurality of acoustical devices adapted to be positioned in fixed positions with respect to the floor of said body of water, and said acoustic transducer and said first and said second plurality of acoustical devices together forming an acoustical network outputting data;

(e) a computer system, said computer system being coupled to said acoustical network, said computer system transforming data from said acoustical into positional data.

25. An in-water ship hull inspection system for inspection of the submerged portion of the hull of a ship floating in a body of water, said inspection system comprising:

(a) a remotely operated vehicle, said remotely operated vehicle comprising:
  (i) a remotely operated vehicle body having a first surface portion, said first surface portion being configured to be oriented towards and supported in a hull inspection position against the hull of a ship to be inspected;
  (ii) a water moving device for moving water located between said first surface portion and said hull of said ship through said remotely operated vehicle body thereby creating a pressure drop between said first surface portion and said hull, said pressure drop being sufficient to result in a force urging said remotely operated vehicle toward said hull;
  (iii) a propulsion mechanism coupled to said body, said propulsion mechanism having at least one thruster, said thruster having the ability to propel said remotely operated vehicle through said body of water toward and onto said hull in said hull inspection position; and
  (iv) a drive mechanism coupled to said remotely operated vehicle body, said drive mechanism having three wheels, at least one said three wheels being driven by a motor to be rotated, when said remotely operated vehicle is in said hull inspection position, rotation of said drive wheels propelling said remotely operated vehicle along said ship hull.

26. An in-water ship hull inspection system as in claim 25, further comprising:

(c) a first plurality of acoustical devices located on the hull of the ship to be inspected, said acoustical devices having fixed positions with respect to said hull;

(d) a second plurality of acoustical devices located in the vicinity of the hull of the ship to be inspected, said second plurality of acoustical devices adapted to be positioned in fixed positions with respect to the floor of said body of water, and said acoustic transducer and said first and said second plurality of acoustical devices together forming an acoustical network outputting data;

(e) a computer system, said computer system being coupled to said acoustical network, said computer system transforming data from said acoustical network into positional data.

27. An in-water ship hull inspection system as in claim 23, further comprising:

(c) a first plurality of acoustical devices located on the hull of the ship to be inspected, said acoustical devices having fixed positions with respect to said hull;

(d) a second plurality of acoustical devices located in the vicinity of the hull of the ship to be inspected, said second plurality of acoustical devices adapted to be positioned in fixed positions with respect to the floor of said body of water, and said acoustic transducer and said first and said second plurality of acoustical devices together forming an acoustical network outputting data;

(e) a computer system, said computer system being coupled to said acoustical network, said computer system transforming data from said acoustical network into positional data.

28. An in-water ship hull inspection system for inspection of the submerged portion of the hull of a ship floating in a body of water, said inspection system comprising:

(a) a remotely operated vehicle, said remotely operated vehicle comprising:
  (i) a remotely operated vehicle body having a first surface portion, said first surface portion being configured to be oriented towards and supported in a hull inspection position against the hull of a ship to be inspected;
  (ii) a water moving device for moving water located between said first surface portion and said hull of said ship through said remotely operated vehicle body thereby creating a pressure drop between said first surface portion and said hull, said pressure drop being sufficient to result in a force urging said remotely operated vehicle toward said hull;
  (iii) a propulsion mechanism coupled to said body, said propulsion mechanism having at least one thruster, said thruster having the ability to propel said remotely operated vehicle through said body of water toward and onto said hull in said hull inspection position; and
  (iv) a drive mechanism coupled to said remotely operated vehicle body, said drive mechanism having a plurality of wheels, at least one said wheels being driven by a motor to be rotated, when said remotely operated vehicle is in said hull inspection position, rotation of said drive wheels propelling said remotely operated vehicle along said ship hull when said remotely operated vehicle is in said hull inspection position, and said drive mechanism being coupled to a thruster prop for driving said vehicle through the water when said vehicle is not in said hull inspection position.

* * * * *